United States Patent
Al Athel et al.

(10) Patent No.: US 6,566,086 B1
(45) Date of Patent: May 20, 2003

(54) DIAGNOSTIC KIT FOR DETECTING CREATINE LEVELS

(75) Inventors: Fahad Mohammed Saleh Al Athel, Riyadh (SA); Thomas W. Bell, Reno, NV (US); Alisher B. Khasanov, Carlsbad, CA (US); Rima Kaddurah-Daouk, Belmont, MA (US)

(73) Assignee: FAL Diagnostics, Portland, OR (US)

( * ) Notice: Subject to any disclaimer, the term of this patent is extended or adjusted under 35 U.S.C. 154(b) by 0 days.

(21) Appl. No.: 09/494,205

(22) Filed: Jan. 28, 2000

(51) Int. Cl.$^7$ ........................... C12Q 1/50; A01N 61/00; A61K 38/00; C07D 221/18; C07D 471/00
(52) U.S. Cl. ............................. 435/17; 514/1; 514/14; 546/26; 546/27; 546/63; 546/73; 546/233
(58) Field of Search ................. 514/1, 14; 546/27, 546/26, 63, 73, 233; 435/17

(56) References Cited

U.S. PATENT DOCUMENTS

| | | | |
|---|---|---|---|
| 4,578,361 A | 3/1986 | Seidel et al. | 436/547 |
| 4,812,399 A | 3/1989 | Mauck et al. | 436/547 |
| 5,030,728 A | 7/1991 | Bell | 546/27 |
| 5,283,333 A | 2/1994 | Bell | 546/27 |

FOREIGN PATENT DOCUMENTS

| | | |
|---|---|---|
| DE | 198 11 196 A | 11/1998 |
| WO | WO 96/34271 A | 10/1996 |

OTHER PUBLICATIONS

Bell, T.W. et al. "Binding biomolecules with designed, hydrogen–bonding receptors" Pure & Applied Chemistry, Dec. 1998, vol. 70(12), pp. 2371–2377 XP000984369.

Bell, T.W. et al. "Complexation of Basic Amino Acid Sidechains by Artificial Receptors" 36$^{th}$ National Organic Symposium, Jun. 13, 1999, Abstract No. 12 XP002174045.

Database WPI Section Ch, Week 198226 Derwent Publications Ltd., London, GB; Class B04, AN 1982–53917E XP002174046 & JP 57 083297 A (Toyobo KK), May 25, 1982 abstract.

Beckles, Daniel L. et al. "Complexation of Creatinine by Synthetic Receptors" *Tetrahedron* 51(2):363–76 (1995).

Bell, Thomas W. and Hou, Zheng "Hydrogen Bonding Chemosensors for Metabolites and Nucleotides" *Chemosensors of Ion and Molecule Recognition* (J.P. Desvergne and A.W. Czarnik eds., Kluwer Academic Publishers, Netherlands) pp. 121–132 (1997).

Bell, Thomas W. and Liu, Jia "Hexagonal Lattice Hosts for Urea. A New Series of Designed Heterocyclic Receptors" *J. Am. Chem. Soc.* 110:3673–74 (1988).

Bell, Thomas W. and Liu, Jia "Torand Synthesis by Trimerization—New Receptors for Guanidinium" *Agnew Chem. Int. Ed. Engl.* 29(8):923–25 (1990).

Bell, T.W. et al. "Detection of Creatinine by a Designed Receptor" *Science* 269:671–74 (1995).

Bell, Thomas W. and Hou, Zheng "A Hydrogen–Bonding Receptor That Binds Urea with High Affinity" *Angew. Chem. Int. Ed. Engl.* 36(13/14):1536–38 (1997).

Bell, Thomas W. et al. "A Small–Molecule Guanidinium Receptor: The Arginine Cork" *Angew. Chem. Int. Ed.* 38(17):2543–48 (1999).

Benedict, Stanley R. "Studies in Creatine and Creatinine Metabolism, II. The Estimation of Creatine" *J. Biol. Chem.* 18:191–94 (1914).

Carey, A.R. Edwin et al. "Keto–Enol and Imine–Enamine Tautomerism of 2–, 3– and 4–Phenacylpyridines" *J. Chem. Soc. Perkin Trans.* 2 2285–96 (1993).

Cram, Donald J. "Preorganization—From Solvents to Spherands" *Angew. Chem. Int. Ed. Engl.* 25(12):1039–1157 (1986).

de Silva, A. Prasanna et al. "New Fluorescent Model Compounds for the Study of Photoinduced Electron Transfer: The Influence of a Molecular Electric Field in the Excited State" *Angew. Chem. Int. Ed. Engl.* 34(16):1728–31 (1995).

Delanghe, J. et al. "Enzymatic creatine determination as early marker for myocardial infarction diagnosis" *Fresnius Z. Anal. Chem.* 330:366–67 (1988).

Dunnett, M. et al. "Reverse–phase ion–pairing high–performance liquid chromatography of phosphocreatine, creatine and creatinine in equine muscle" *Scand. J. Clin. Lab. Invest.* 51:137–41 (1991).

Fossati, Piero et al. "Enzymatic Creatinine Assay: A New Colorimetric Method Based on Hydrogen Peroxide Measurement" *Clin. Chem.* 29(8):1494–96 (1983).

Harris, R.C. et al. "Glycogen, Glycolytic Intermediates and High–Energy Phosphates Determined in Biopsy Samples of Musculus Quadriceps Femoris of Man at Rest. Methods and Variance of Values" *Scand. J. Clin. Lab. Invest.* 33:109–20 (1974).

Hughes, Martin P. et al. "High Affinity Carboxylate Binding Using Neutral Urea–Based Receptors with Internal Lewis Acid Coordination" *J. Org. Chem.* 61(14):4510–11 (1996).

Hung, Yiau–Lin et al. "High–Performance Liquid Chromatographic Analyser for Guanidine Compounds Using Benzoin as a Fluorogenic Reagent" *J. Chromatography* 305:281–94 (1984).

Jaynes, Patrick K. et al. "An Enzymic, Reaction–Rate Assay for Serum Creatinine with a Centrifugal Analyzer" *Clin. Chem.* 28(1):114–17 (1982).

(List continued on next page.)

Primary Examiner—Jezia Riley
(74) Attorney, Agent, or Firm—Lahive & Cockfield, LLP; Elizabeth A. Hanley, Esq.; Cynthia M. Soroos

(57) ABSTRACT

Methods for the detection of creatine compound levels in body fluid samples are discussed. Portable kits capable of determining creatine levels using non-invasive and visually detectable methods are also included.

33 Claims, No Drawings

OTHER PUBLICATIONS

Jeppsen, Mette Tranholm. and Hansen, Elo Harald "Determination of Creatinine in Undiluted Blood Serum by Enzymatic Flow Injection Analysis with Optosensing" *Analytica Chimica Acta* 214:147–59 (1998).

Johnson, Dianne "Evaluation of Renal Function" in *Clinical Chemistry* (E. Howard Taylor ed., John Wiley & Sons, Inc., NY) 55–82 (1989).

Jurkiewicz, M. et al. "Development of a biparametric bioanalyzer for creatinine and urea. Validation of the determination of biochemical parameters associated with hemodialysis" *Analyst* 123:1321–27 (1988).

Kinoshita, Hideaki et al. "Peroxidase–Based Amperometric Sensor of Hydrogen Peroxide Generate in Oxidase Reaction: Application to Creatinine and Creatine Assay" *Electroanalysis* 9(16):1234–38 (1997).

Mădăras, Marcel B. et al. "Microfabricated amperometric creatine and creatinine biosensors" *Analytica Chimica Acta* 319(3):335–45 (1996).

Mădăras, Marcel B. and Buck, Richard P. "Miniaturized Biosensors Employing Electropolymerized Permselective Films and their Use for Creatinine Assays in Human Serum" *Anal. Chem.* 68(21): 3832–39 (1996).

McCann, Geraldine M. et al. "Proton activating factors and keto–enol–zwitterion tautomerism of 2–,3– and 4–phenylacetylpyridines" *J. Chem. Soc. Perkin Trans.* 2 2761–72 (1997).

Metzger, Axel et al. "Molecular Recognition and Phase Transfer of Underivatized Amino Acids by a Foldable Artificial Host" *J. Org. Chem.* 61:2051–55 (1996).

Moss, Gerald A. et al. "Kinetic Enzymatic Method for Determining Serum Creatinine" *Clin. Chem.* 21(10):1422–26 (1975).

Motesharei, Kianoush and Myles, David C. "Molecular Recognition in Membrane Mimics: A Fluorescence Probe" *J. Am. Chem. Soc.* 116(16):7413–14 (1994).

Motonaka, J. et al. "Preparation and Properties of a Micro Enzyme Sensor for Creatine" *Anal. Lett.* 23(11):1981–91 (1990).

Okumiya, Toshika et al. "Sensitive enzymatic assay for erythrocyte creatine with production of methylene blue" *Clin. Chem.* 44(7):1489–96 (1998).

Werner, G. et al. "Simultaneous Determination of Creatine, Uric Acid and Creatinine by High–Performance Liquid Chromatography with Direct Serum Injection and Multi–Wavelength Detection" *J. Chromatography* 525:265–75 (1990).

Wilcox, Craig S. et al. "Experimental and Theoretical Studies of Substituent Effects in Hydrogen Bond Based Molecular Recognition of a Zwitterion by Substituted Arylureas" *Tetrahedron* 51(2):621–34 (1995).

DIAGNOSTIC KIT FOR DETECTING CREATINE LEVELS

BACKGROUND OF THE INVENTION

Creatine is a naturally occurring compound. Both creatine and its phosphorylated form, creatine phosphate, are found in mammalian brains, skeletal muscles, retinas, hearts, and other excitable tissues. Creatine, creatine phosphate and the enzymes that utilize them as substrates, i.e., the creatine kinases, represent an efficient system for the rapid regeneration of energy. Creatine phosphate is the product of the creatine kinase reaction which uses creatine as a substrate. Creatine and creatine phosphate can be chemically synthesized relatively easily and are believed to be non-toxic to mammals.

The creatine kinase/creatine phosphate energy system is one component of an elaborate energy-generating system found in body tissues such as nervous tissues and muscle cells (see, for example, Wallimann, *Biochem J.* (1992) 281:21–40). The components of the creatine energy system include the enzyme creatine kinase, the substrates creatine and creatine phosphate, and the creatine transporter. Functions associated with this pathway include regeneration of energy in cells with fluctuating and high energy demands, energy transport to different parts of the cell, phosphoryl transfer activity, ion transport regulation, and signal transduction pathways involvement.

It is believed that creatine phosphate initially buffers ATP hydrolysis by regenerating ATP during high-intensity exercise. When present, creatine phosphate is thought to delay both the induction of glycolysis and the stimulation of mitochondrial oxidative phosphorylation. Unfortunately, creatine phosphate is typically depleted within ten seconds because of limited stores in muscle. Therefore, it is hypothesized that muscle performance may be favorably affected by increasing the muscle stores of creatine and creatine phosphate and, thus, delaying the depletion of creatine phosphate.

Within the last several years, creatine supplementation as an ergogenic aid has increased (for reviews, see Balsom et al., *Sports Med.* (1994) 18(4):268–80; Greenhaff, et al. Int. *J. Sport Nutr.* (1995) Suppl:S100–110; Maughan, et al. *Int. J. Sport Nutr.* (1995) 5(2):94–101). Currently, there is widespread enthusiasm by many top athletes about the performance-boosting effects of creatine. Creatine supplementation is popular in many explosive sports such as bodybuilding, tennis, cycling, mountain biking, rowing, ski-jumping, fencing, cross-country skiing, down-hill skiing, rugby, handball, basketball, football and hockey.

Creatine oral supplementation has been shown to result in improved cell energy profiles. Improved energy profiles protect the function of cells (e.g., neural or muscle cells) by preventing oxidative damage, aberrant cell metabolism, and cell death. The improved energy profiles may be beneficial for treatment of aging by minimizing cell damage and death. Creatine and creatine compounds also may be able to be effective in other diseases which involve defective metabolic pathways, such as diabetes, obesity, and bone density related disorders.

Therapeutic uses of creatine and related compounds include the use of creatine compounds to treat neurodegenerative diseases such as Huntington's, Parkinson's, and ALS (WO 96/14063). In animal models of Huntington's disease, oral supplementation of either creatine or cyclocreatine was shown to protect the animals from malonate lesions (Matthews et al., *J Neurosci.* (1998) 18(1):156–63).

Creatine supplementation has also been found to be useful for protecting against 3-NP neurotoxicity. Creatine has been shown to protect against MPTP-induced loss of neurons in the substantia nigra and prevented loss of dopamine and its derivatives in animal models of Parkinson's disease (Matthews et. al., *Exp. Neurol.* (1999) 157(1):142–149). Furthermore, it was found that creatine both protects animal models from oxidative stress and improves their energy profiles. In an animal model of amyotrophic lateral sclerosis (ALS), creatine supplementation was shown to extend survival of subjects, improve their motor performance, and protect them against loss of motor neurons (Kliveny et.al, *Nat Med.* (1999) 5(3):347–50).

Creatine and creatine compounds have also been used in other therapeutic methods. For example, cyclocreatine has been found to restore functionality in muscle tissue (U.S. Pat. No. 5,091,404). Creatine and creatine compounds have been shown to inhibit cancers and the growth of certain tumors (WO94/16687; U.S. Pat. Nos. 5,324,731; 5,676, 978); treat weight and energy related disorders, such as obesity; treat glucose related disorders, such as diabetes (WO 97/13507); and treat viral infections (U.S. Pat. No. 5,321,030). Creatine compounds have also been shown to increase bone density.

SUMMARY OF THE INVENTION

In one embodiment, the invention pertains to a method for determining creatine compound levels in a body sample of a subject. The method includes contacting a body sample with a creatine sensing substance, and analyzing the resulting mixture. Examples of preferred body samples include, for example, body fluids such as blood, saliva, sweat and urine. In an advantageous embodiment, the body sample is obtained non-invasively. In a particularly preferred embodiment, the creatine compound level is analyzed through a color change, e.g., a change in optical characteristics or fluorescence, of the creatine sensing substance and body fluid mixture. In a further embodiment, the method includes the step of administering a creatine compound to a subject. The subject may have, for example, sub-optimum creatine levels through out his entire body; sub-optimum levels in certain organs or areas (e.g., muscles or brain); or normal or above average creatine levels.

The invention also pertains to a kit suitable for determining creatine compound levels in a subject. Preferably, the kit includes directions for use. In one embodiment of the kit, the creatine sensing substance is embedded in a solid, permeable substrate. In another embodiment the kit includes a vial for mixing a creatine sensing substance with a body sample.

The invention further pertains to methods for comparing creatine levels to creatinine levels. The method includes contacting a body fluid of the subject with a creatine sensing compound and a creatinine sensing compound, and analyzing the resulting mixture. In one embodiment, the subject is suffering from kidney dysfunction. In another embodiment, the subject had previously been administered a creatine compound.

DETAILED DESCRIPTION OF THE INVENTION

The invention pertains, at least in part, to methods and kits for determining levels of creatine compounds in a body sample. In one embodiment, the invention pertains to a diagnostic kit that can detect levels of creatine compounds in body sample. The invention includes methods for determining the appropriate levels of a creatine compound, to administer to a subject who may be suffering from aberrant creatine compound levels due to disease or the aging process, or to a subject, for example, who may wish to optimize his creatine compound levels for its beneficial effects.

Creatine (also known as N-(aminoiminomethyl)-N-methylglycine; methylglycosamine or N-methyl-guanido acetic acid) is a well-known substance. (See, The Merck Index, Eleventh Edition, No. 2570 (1989)). Creatine can be phosphorylated chemically or enzymatically by creatine kinase to generate creatine phosphate (see, The Merck Index, No. 7315). Both creatine and creatine phosphate (phosphocreatine) can be extracted from animal tissue or synthesized chemically. Both are commercially available. Cyclocreatine is an essentially planar cyclic analog of creatine, which can be phosphorylated efficiently by creatine kinase both in vitro and in vivo. Although cyclocreatine is structurally similar to creatine, the two compounds are distinguishable both kinetically and thermodynamically (Rowley, G. L., *J. Am. Chem. Soc.* (1971) 93:5542–5551; McLaughlin, A. C. et. al., *J. Biol. Chem.* (1972) 247:4382–4388).

The term "creatine compounds" includes creatine, creatinine, creatine phosphate, and compounds which are structurally similar to creatine or creatine phosphate, and analogs of creatine and creatine phosphate. Examples of creatine compounds include, for example, cyclocreatine (1-carboxymethyl-2-iminoimidazolidine), N-phosphorocreatine (N-phosphoryl creatine), and cyclocreatine phosphate (3-phosphoryl-1-carboxymethyl-2-iminoimidazolidine). In addition, 1-carboxymethyl-2-aminoimidazole, 1-carboxymethyl-2 2-iminomethylimidazolidine, 1-carboxyethyl-2-iminoimidazolidine, N-ethyl-N-amidinoglycine, b-guanidinopropionic acid, creatine-pyruvate and creatine-ascorbate are also included. In one embodiment, the term "creatine compounds" does not include creatinine. Preferred creatine compounds include creatine phosphate, cyclocreatine, cyclocreatine phosphate, and, especially preferred, creatine.

Creatine, creatine phosphate and many creatine analogs are commercially available. Additionally, analogs of creatine may be synthesized using conventional techniques. Appropriate synthesis reagents, e.g. alkylating, alkenylating or alkynylating agents may be used to attach the respective groups to target sites. Alternatively, reagents capable of inserting spacer groups may be used to alter the creatine structure. Sites other than the target site are protected using conventional protecting groups while the desired sites are being targeted by synthetic reagents. Creatine analogs containing ring structures can be synthesized using procedures analogous to that described for cyclocreatine (Wang, T., *J. Org, Chem*, 39:3591–3594 (1974)). The various other substituent groups may be introduced before or after the ring is formed.

Many creatine analogs have been previously synthesized and described (Rowley et al., *J. Am. Chem. Soc.* 93:5542–5551 (1971); McLaughlin et al., *J. Biol. Chem.* 247:4382–4388 (1972); Lowe et al., *J. Biol. Chem.* 225:3944–3951 (1980); Roberts et al., *J. Biol. Chem.* 260:13502–13508 (1985); Roberts et al., *Arch. Biochem. Biophys.* 220:563–571 (1983), Griffiths et al.,*J. Biol. Chem.* 251:2049–2054(1976), WO92/08456, WO90/09192, U.S. Pat. Nos. 5,324,731, 5,321,030, 5,998,457). The contents of all of the aforementioned references are expressly incorporated by reference.

Creatine compounds which currently are available or have been synthesized include, for example, creatine, β-guanidinopropionic acid, guanidinoacetic acid, creatine phosphate disodium salt, cyclocreatine, homocyclocreatine, phosphinic creatine, homocreatine, ethylcreatine, cyclocreatine phosphate dilithium salt, guanidinoacetic acid phosphate disodium salt, creatine-pyruvate and creatine ascorbate, among others.

Creatine analogs may have therapeutic benefits. Ingestion of creatine analogs has been shown to result in replacement of tissue phosphocreatine pools by synthetic phosphagens with different kinetic and thermodynamic properties. This results in subtle changes of intracellular energy metabolism, including the increase of total reserves of high-energy phosphate (Roberts, J. J. et al., *Arch Biochem. Biophys* (1983) 220(2):563–571). The replacement of phosphocreatine pools with slower acting synthetic phosphagens, such as creatine analogs might benefit neurological disorders by providing a longer lasting source of energy. Cyclocreatine is believed to modify the flow of energy of cells in stress and may interfere with ATP utilization at sites of cellular work.

In one embodiment, the invention pertains to a method for determining creatine compound levels in a body sample. The method includes contacting a body sample with a creatine sensing substance, and analyzing the resulting mixture. Preferably, the creatine sensing substance is a creatine recognizing substance.

The term "body sample" includes body fluids and tissues which may potentially contain creatine compounds. Advantageously, the body sample contains creatine compounds in levels which are proportionate to the creatine level in body tissues which utilize the creatine kinase energy system (e.g., muscle, brain, nervous system, etc.). The body sample can be obtained invasively, but preferably, the body sample is obtained through non-invasive methods. Examples of body samples include, for example, tissues which utilize the creatine kinase energy system. Examples of such tissues include muscle, brain, nervous tissue, retina tissue, and kidney tissue. Furthermore, the term "body sample" also includes body fluids. The term "body fluids" includes all fluids obtained from a mammalian body, including, for example, blood, plasma, urine, serum, saliva, sweat, and spinal and brain fluids. In a preferred embodiment, the creatine compound is creatine. Furthermore, the body sample may be either processed (e.g., serum, crushed cellular material) or unprocessed.

The language "creatine compound level" includes the amount or concentration of creatine compounds in a body sample. Preferably, the creatine compound level of the body sample is indicative of the concentration of creatine compounds in the body, a specific body tissue, or preferably, in a body tissue which utilizes the creatine kinase energy system. Advantageously, the concentration of the creatine in the body can be extrapolated from the creatine compound level determined through the methods and kits of the invention. The invention includes methods and kits which detect the presence or absence of a creatine compound concentration over a certain threshold concentration, which may, advantageously, be adjusted based on the optimal or advantageous creatine compound concentrations for a particular situation or a particular patient. For example, the certain threshold concentration of a creatine compound may be individual to a user or to a group of users, e.g., elderly people, athletes, obese people, patients with neurological disorders, etc. In another embodiment, the invention includes methods and kits which detect relative or absolute concentrations of creatine compounds in a body sample. In a preferred embodiment, the creatine compound level is the level of creatine in a body sample.

Determination of the creatine compound levels in body tissues such as muscles may be relevant to patients, athletes, and scientists studying creatine supplementation. It has been recognized that oral creatine supplementation can increase the muscle concentration of total creatine (e.g., Crim et al., *J Nutr.* (1975) 105(4):428–38). Currently, creatine supplementation most commonly involves a "loading phase" of 5–7 days where 20–30 g of creatine monohydrate are consumed per day, and a "maintenance phase" with 2–3 g creatine per day. These values may be compared with a hypothesized daily creatine requirement of 2 g which is generally provided by a combination of diet and de novo biosynthesis. Creatine loading with 20–30 g/day has been shown to significantly increase the muscle concentrations of creatine, creatine phosphate and total creatine (Harris et al., *Clin Sci (Colch).* (1992) 83(3):367–74; Greenhaff et al., *Am J Physiol.* (1994) 266(5):E725–730; Greenhaff et al. *Clin Sci (Colch).* (1993) 84(5):565–71; Febbraio et al., *Acta Physiol Scand.* (1995) 155(4):387–95; Gordon et al., *Cardiovasc Res.* (1995) 30(3):413–8; Green et al., *Am J Physiol.* (1996) 271 :(5):E821–6; Hultman et al., *J Appl Physiol.* (1996) 81(1):232–7; Vandenberghe et al., *J Appl Physiol.* (1997) 83(6):2055–63). Large individual differences have been noted for both initial creatine concentration and responsiveness to creatine supplementation. However, increases in total creatine level have been observed in subjects with low initial creatine levels (e.g., from 114 to 156 mmol/kg dry mass). Exercise may also stimulate creatine uptake into muscle (Greenhaff, *Int J Sport Nutr.* (1995) 5 Suppl:S100–10). Simultaneous carbohydrate ingestion also may also augment creatine retention in muscle (Green et al., *Acta Physiol Scand.* (1996) 158(2):195–202).

In other studies, it has been shown that insulin may stimulate creatine uptake in rat skeletal muscle and mouse myoblasts (Koszalka et. al., *Proc Soc Exp Biol Med.* (1972) 139(4):1265–71; Haugland et al., *Proc Soc Exp Biol Med.* (1975) 148(1):1–4; Odoom et al., *Mol Cell Biochem.* (1996) 158(2):179–88). Creatine supplementation has been shown to increase the urinary excretion of creatinine which is believed to be consistent with elevated muscle concentrations of creatine and creatine phosphate (Rossiter et al. *J Sports Sci.* (1996) 14(2): 175–9).

The language "total creatine level" includes the sum of the levels of all creatine compounds in a subject. In one embodiment, the total creatine level may be the sum of a subject's creatine, creatinine, and creatine phosphate levels.

In a further embodiment, the creatine compound level can be compared to the level of creatinine in a body sample. For example, hospital based assays currently use creatinine levels as a method for diagnosing kidney dysfunction. The invention includes a method for comparing creatine and creatinine levels in a body sample, which may, advantageously, for example, potentially indicate kidney dysfunction or whether creatine supplementation leads to increased creatinine in a body fluid. In this method, a creatinine assay is used to determine creatinine levels and a creatine assay is used to determine creatine levels. Preferably, the creatine assay is an assay of the present invention and is specific for creatine. By comparing the results of the assays, a person may be able to determine whether elevated levels of creatinine are due to kidney dysfunction or by elevated creatine levels, e.g., due to creatine supplementation or administration.

The term "creatine sensing substance" includes substances which interact with creatine compounds, such that creatine compounds levels in a body sample can be determined. Advantageously, the determination of the creatine compound level is discernible without the use of laboratory equipment. For example, in an advantageous embodiment, the creatine sensing substance interacts with the creatine compound in a body sample such that the creatine compound level can be determined visually, e.g., by a change in color, hue or intensity of the mixture of the body sample and the creatine sensing substance. The term "laboratory equipment" includes HPLC, fluorometers, spectrometers (NMR, IR), optical density meters, etc. The term "laboratory equipment" does not include charts or other tables which involve visual comparison of a solution to the chart or table, equipment (e.g., refrigerator, freezer, scissors) usually found in a home, or equipment, e.g., a solution vial, dish, or a syringe, which can be reasonably packaged with the kit without prohibitive expense to the user or another.

In other embodiments, the determination of creatine compound levels include additional steps, such as, exposing the mixture to radiation of appropriate wavelength to observe fluorescence. Furthermore, additional substances may be used to detect the presence of an interaction between the creatine sensing substance and a creatine compound. Preferably, the creatine sensing substance interacts specially with creatine phosphate, cyclocreatine, cyclocreatine phosphate, and, in an especially preferred embodiment, creatine. In one embodiment, the creatine sensing substance comprises a polypeptide, e.g., an antibody or a fragment thereof, which binds to creatine compounds. In another embodiment, the creatine sensing substance comprises a cage molecule, such as, for example, a fullerene. Advantageously, the creatine sensing substance specifically interacts with a specific creatine compound, for example, creatine. Furthermore, the term "creatine sensing substances" includes "creatine recognizing substances."

The term "creatinine sensing substance" includes substances which interact with creatinine, such that the concentration or amount of creatinine in a body sample can be determined. Creatinine sensing substances also include substances known in the art for determining creatinine levels. Examples of creatinine sensing substances include enzymes, such as creatinine deiminase (aminohydrolase) (Jurciewicz, et al. *Analyst* (1998) 123:1321–1327; Jeppsen et al. *Analytica Chimica Acta* (1998) 214:147–159), the creatinine amidohydrolase/creatine kinase/pyruvate kinase/lactate dehydrogenase system (Jaynes et al. *Clin. Chem.* (1982)28 (1):114–117; Moss et al. *Clin. Chem.* (1975) 21(10): 1422–1426), and the creatininase/creatinase/sarcosine oxidase system (Madaras et al. *Anal. Chem. Acta.* (1996) 319(3):335–345; Madaras et al. *Anal. Chem.* (1996) 68(21): 3832–3839; Fossati et al. *Clin. Chem.* (1983) 29(8): 1494–1496). Other methods of determining creatinine levels include the Jaffe reaction, which is a colorimetric reaction using alkaline picrate (see, "Evaluation of Renal Function" in *Clinical Chemistry* (E. H. Taylor, Ed.) Wiley, NY (1989) pp. 55–82). Other creatinine sensing substances interact with creatinine resulting in an optical change (Bell, T. W. et al. *Science* (1995) 269:671–674). Furthermore, creatinine levels in a sample can also be determined using other methods such as chromatographic techniques.

The term "creatine recognizing substances" includes substances which specifically interact with creatine compounds. The creatine recognizing substances may be specific for certain creatine compounds, e.g., creatine, creatine phosphate, cyclocreatine phosphate, cyclocreatine, or salts or ions thereof. The interaction of creatine compounds with creatine recognizing substances can be detected without modification of the creatine or creatine compound, or the production of an enzymatic product. However, deprotonation or protonation of acidic or basic groups of creatine compounds is not considered to be modification of the creatine compounds.

Creatine recognizing substances involve specific interactions between the substances and the creatine compounds. The language "specifically interact" or "specific interactions" is not intended to include general methods of separation and detection, such as chromatographic techniques (e.g., HPLC) which use, for example, molecular weight, charge, or vaporization point to separate molecules with similar physical properties. The language "specifically interact" or "specific interactions" includes interactions between the creatine recognizing substance and the creatine compound which are capable of identifying the creatine compound based on its structural properties on a molecular level, such as the size, location and polarity of chemical moieties of the creatine compound. Furthermore, the term "creatine sensing substances" includes "creatine recognizing substances." In a preferred embodiment, the creatine recognizing substance specifically interacts with cyclocreatine, cyclocreatine phosphate, creatine phosphate, and, in a particularly preferred embodiment, creatine.

Examples of creatine recognizing substances include, for example, antibodies which detectably interact with creatine compounds and other organic and organometallic molecules. In another embodiment, the creatine recognizing compound does not specifically interact with creatinine.

In a preferred embodiment, the creatine recognizing substance is an organic small molecule. The term "organic small molecule" includes organic and organo-metallic molecules. In one embodiment, the organic small molecules of the invention interact with creatine compounds such that the presence or concentration of creatine compounds in a sample can be determined.

Over the past 30 years, chemists have designed and synthesized many organic compounds capable of interacting with other organic molecules. These organic compounds are also termed "host" compounds or "artificial receptors" by analogy with biological receptors that bind and recognize "guests." "Host-guest" or supramolecular chemistry, has numerous biomedical applications, including detection and quantitation of analytes, such as creatine compounds, in biological fluids. In one embodiment, the invention includes "host" creatine sensing substances which interact with creatine compounds.

Examples of using "host-guest" supramolecular chemistry include interactions between urea "guests" and diketone "hosts" as previously described (Bell, T. W. et al. *J. Am. Chem. Soc.* (1988) 110:3673–3674). The strength of this complex was thought to be due to the relative rigidity of the diketone "host" prior to interaction with the urea, and the position of the diketone's hydrogen-bond acceptor nitrogen and oxygen atoms in nearly ideal locations to form strong hydrogen bonds with the creatine compound's NH stabilizing groups. The principle of preorganization includes both the effect of the conformational organization of the host and the low solvation of the binding site before complexation (Cram, D. J. *Angew. Chem. Int. Ed. Engl.* (1986) 25:1039–1134). Other series of highly preorganized hydrogen bonding receptors for various guest molecules have been also synthesized and discussed (Bell, T. W. et al. *Angew. Chem. Int. Ed. Engl.* (1997) 36:1536–1538; Bell, T. W. et al. *Angew. Chem. Int. Ed. Engl.*, (1990) 29:923–925; Beckles, D. L. et al. *Tetrahedron* (1995) 51:363–376; U.S. Pat. Nos. 5,030,728; and 5,283,333).

In one embodiment, the creatine recognizing substance includes at least one aromatic ring or conjugated π-bond system. The aromatic ring may be, for example, heteroaryl, e.g., pyridyl, pyrazinyl. Advantageously, the creatine sensing substance may be multicyclic. For example, the creatine sensing system may include at least one conjugated aromatic moiety.

In one embodiment, the creatine recognizing substance is comprised of at least one rigid coordinating moiety capable of coordinating to a creatine compound (Cr).

The term "rigid coordinating moiety" includes moieties which coordinate with a creatine compound. Preferably, the rigid coordinating moiety detectably coordinates with creatine compounds at biological concentrations. The rigid coordinating moiety can be advantageously designed to specifically interact with certain creatine compounds, e.g., creatine, creatine phosphate, cyclocreatine, or cyclocreatine phosphate. Advantageously, the rigid coordinating moiety is multicyclic, and may advantageously contain at least one heterocycle, e.g., a nitrogen containing heterocycle, e.g., a pyridyl moiety. Examples of rigid coordinating moieties include the following structures shown below.

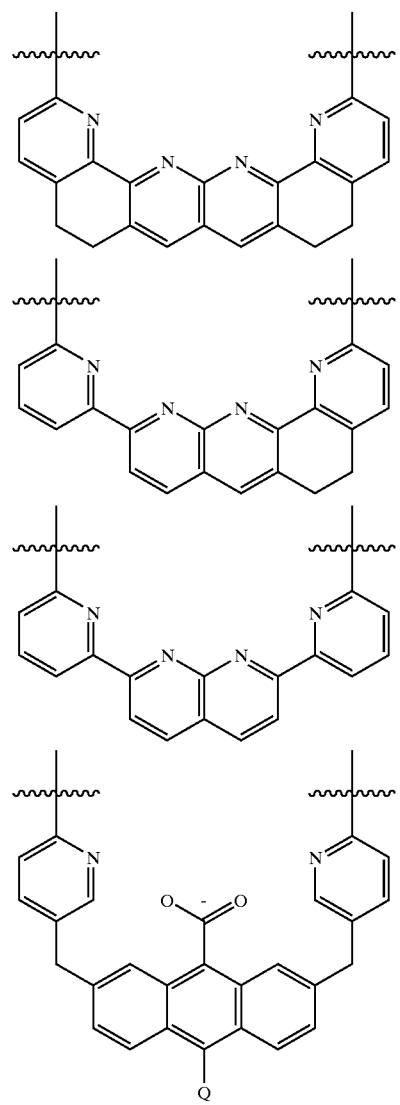

-continued

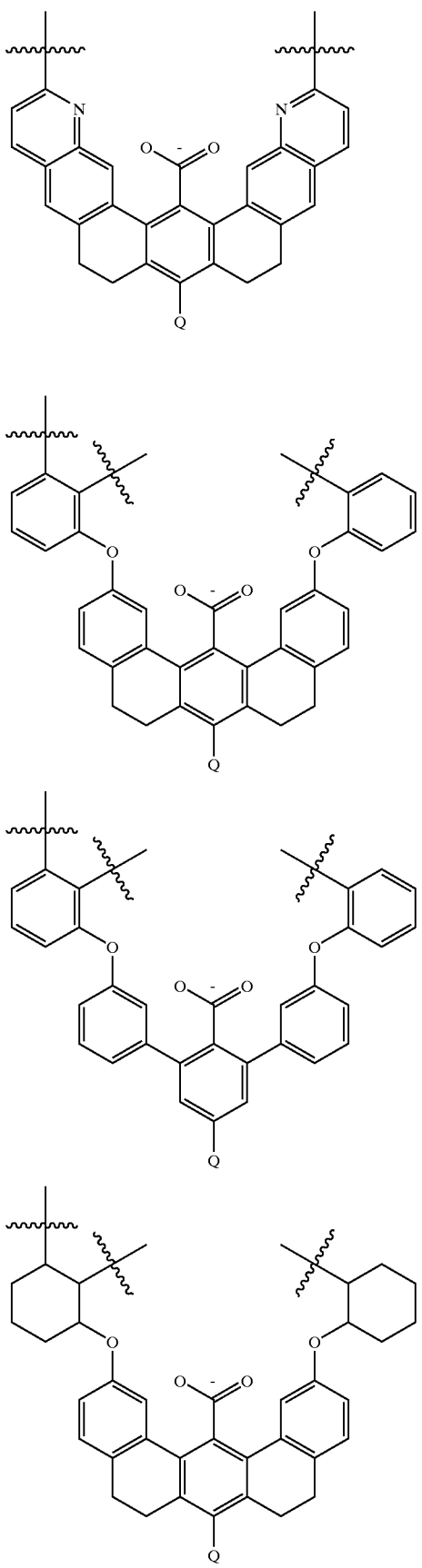

-continued

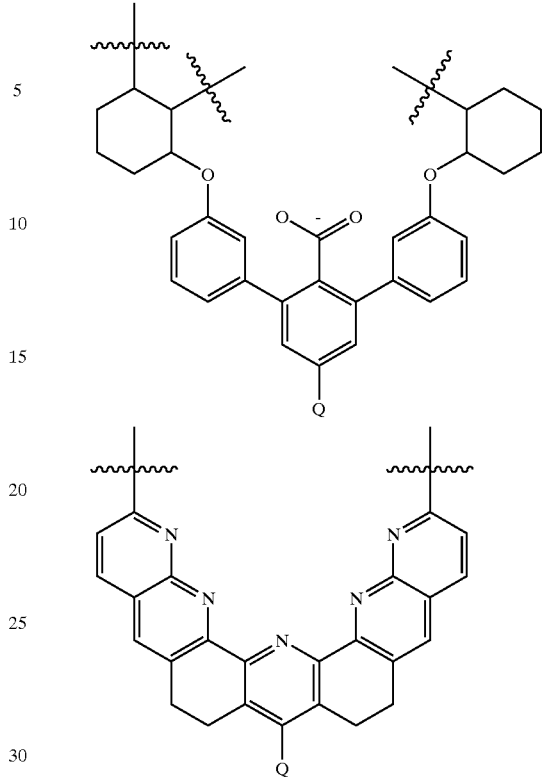

wherein Q is alkyl, alkenyl, alkynyl, hydrogen, halogen, or another atom or moiety which allows the rigid coordinating moiety to perform its intended function.

Furthermore, other examples of rigid coordinating moieties include derivatives and analogs of the rigid coordinating moieties shown above. For example, the rigid coordinating moieties shown above can be substituted with various functional groups to enhance their ability to perform their function, e.g., detect creatine compound levels.

Analogs include, for example, compounds and moieties which are structurally similar but may have substitutions of heteroatoms or other changes which do not prohibit the rigid coordinating moiety or the creatine recognizing substance from performing its intended function, e.g., determine creatine compound levels in a body sample. In an advantageous embodiment, the analogs or derivatives of the rigid coordinating moieties shown above enhance the ability of the creatine recognizing compound to perform its intended function.

For example, in an advantageous embodiment, the rigid coordinating moiety may further comprise a chromophore (e.g., heterocyclic, carbocyclic, or not cyclic) or a fluorophore. In one embodiment, the chromophore may be incorporated into the interaction site of the creatine compound of interest of the creatine recognizing substance. Rigid coordinating moieties of the invention may be conducive to the design of creatine sensing substances which change optical properties upon complexation of creatine compound of interest. The inclusion of a chromophore or fluorophore may advantageously enhance communication between interaction of the creatine compound with the creatine recognizing compound and signal transduction (*Chemosensors of Ion and Molecule Recognition,* J. P. Desvergne, A. Czarnik, Eds., Kluwer:Dordrecht, The Netherlands, 1997, pp. 121–132).

In a further embodiment, the creatine recognizing substance may also include acceptor groups (A) and stabilizing groups (D). The acceptor groups and stabilizing groups include groups which enhance the ability of the creatine recognizing substance to perform its function, e.g., recognize a creatine compound. Advantageously, the creatine recognizing substance is of the formula (I):

$$R(A)_n(D)_m \qquad (I)$$

wherein D is a stabilizing group, A is an acceptor group, and n and m are integers independently selected such the creatine recognizing substance is capable of performing its intended function, e.g., recognizing creatine compounds. For example, n and m may each be integers between 0 and 15. The integers n and m are further selected to allow a plurality of groups A and/or D. The integer n is preferably about 0 to about 10, more preferable about 0 to about 5, even more preferably about 1 to about 2. The integer m is preferably about 0 to about 10, more preferable about 0 to about 5, even more preferably about 1 to about 2. The ranges of n and m values intermediate to those listed also are intended to be part of this invention, e.g. about 1 to 14, about 3 to 9, and about 4 to about 8. For example, ranges of n and m values using a combination of any of the above values recited as upper and/or lower limits are intended to be included.

In one embodiment the creatine recognizing substance is of the formula:

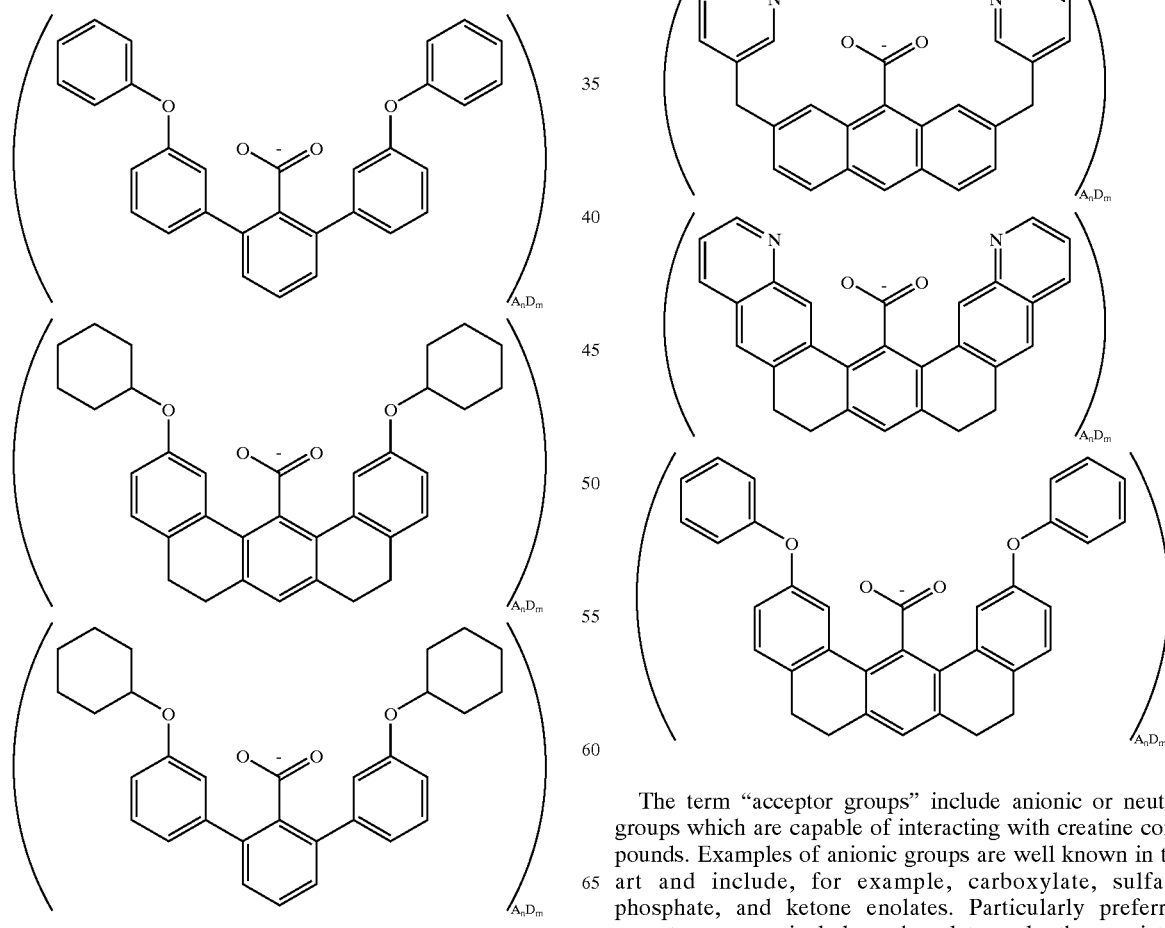

The term "acceptor groups" include anionic or neutral groups which are capable of interacting with creatine compounds. Examples of anionic groups are well known in the art and include, for example, carboxylate, sulfate, phosphate, and ketone enolates. Particularly preferred acceptor groups include carboxylate and other moieties capable of forming hydrogen bonds with the amino groups of creatine compounds.

In a further embodiment, the creatine recognizing substance is of formula (II):

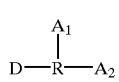

(II)

wherein $A_1$ and $A_2$ are acceptor groups, R is a rigid coordinating moiety and D is a stabilizing group.

In one embodiment, $A_2$ is carboxylate. In an advantageous embodiment, $A_1$ is selected from the group consisting of:

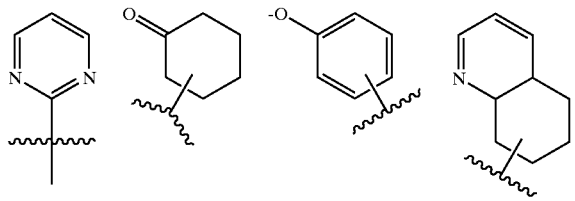

The term "stabilizing groups" include groups which allow the creatine recognizing substance to interact with creatine compounds. Advantageously, the stabilizing group interacts with the carboxylate group of creatine. In one embodiment, D is neutral or cationic. In a further embodiment, D comprises at least one nitrogen containing group. Examples of stabilizing groups include:

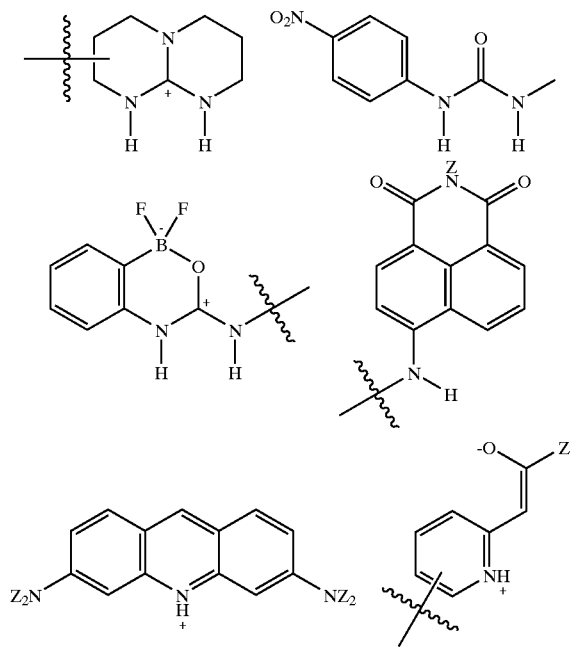

wherein Z is alkyl, alkenyl, alkynyl, hydrogen, acyl, hydrogen, and halogen atoms.

The structure of the stabilizing group D and its linkage to the bottom part of the receptor can be tailored to produce optimal binding and optical signal transduction. Structures 1–3 show three examples of stabilizing groups that can be incorporated into the receptor structure and are known to form strong complexes with carboxylate groups

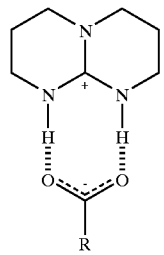

1

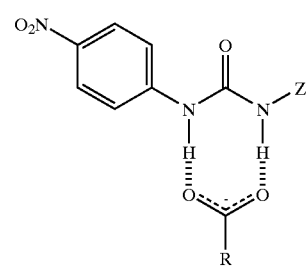

2

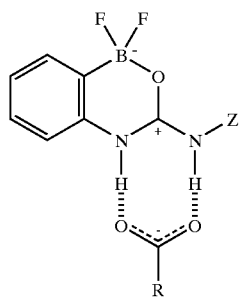

3 via two hydrogen bonds. The bicyclic guanidinium group in 1 remains protonated at most biologically relevant pH values and forms a strong electrostatic contact with the carboxylate group (Metzger, A.; *J. Org. Chem.* (1996) 61:2051–2055). para-Nitrophenyl substituted ureas, as shown in 2, are uncharged but also bind carboxylates via two hydrogen bonds (Wilcox, C. S. *Tetrahedron* (1995) 51:621–634). In 3, cyclic coordination of a boronate ester with a urea group forms a dipolar structure having high affinity for carboxylate anions (Hughes, M. P. et al. *J. Org. Chem.* (1996) 61:4510–4511). Stabilizing group D can also be replaced by a polydentate ligand capable of binding a metal cation, providing an electrostatic or coordination contact with the carboxylate group of creatine. Analogs and derivatives of the stabilizing groups mentioned above are also included.

In one embodiment, the creatine recognizing substance is selected from the group consisting of the following compounds and derivatives and analogs thereof. For example, a person of ordinary skill in the art can appreciate that the compounds depicted below can be substituted with numerous functional groups to enhance their ability to perform their intended function. Furthermore, equivalent molecules can be synthesized which have similar characteristics. All equivalent molecules which are potentially useful as creatine sensing or recognizing compounds are included herein.

15
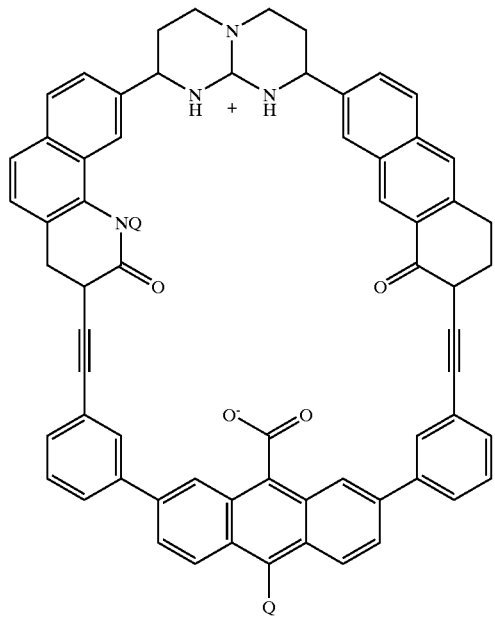
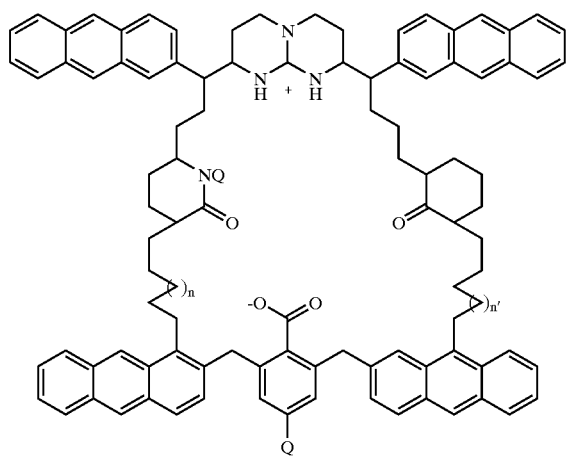
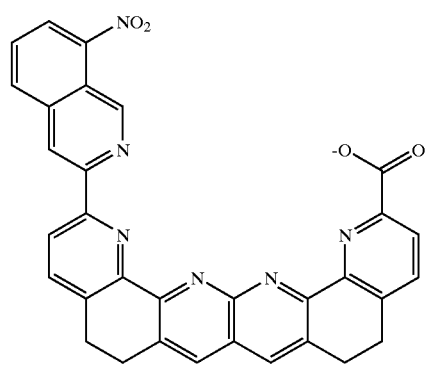
16
-continued
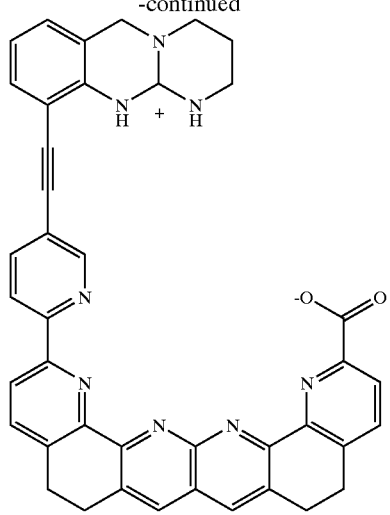
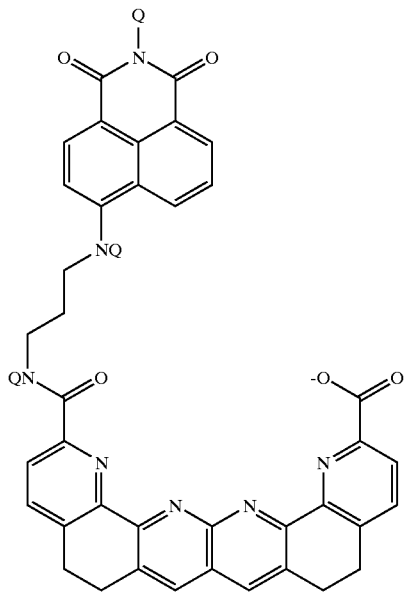
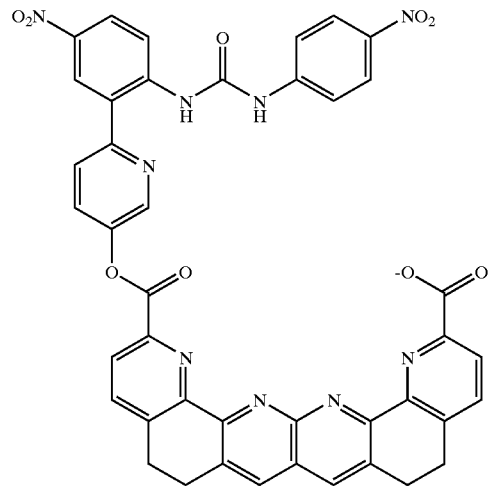

17
-continued
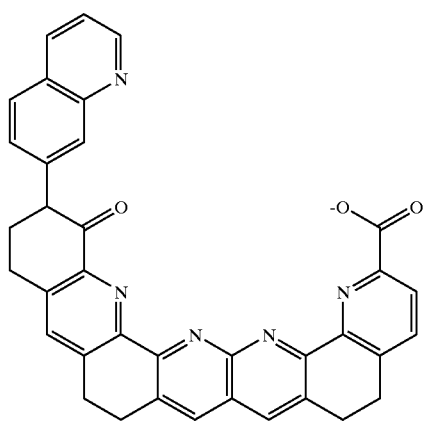
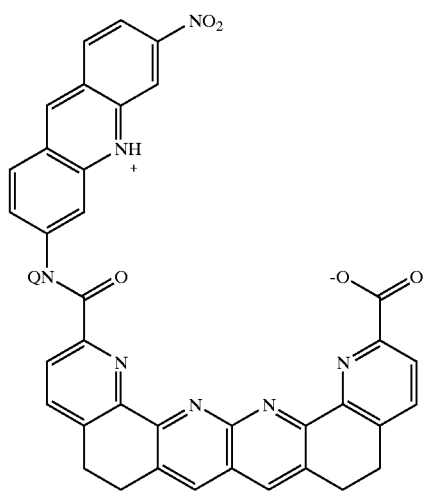
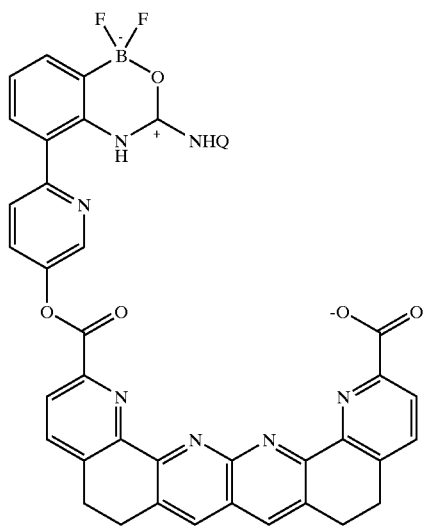
18
-continued
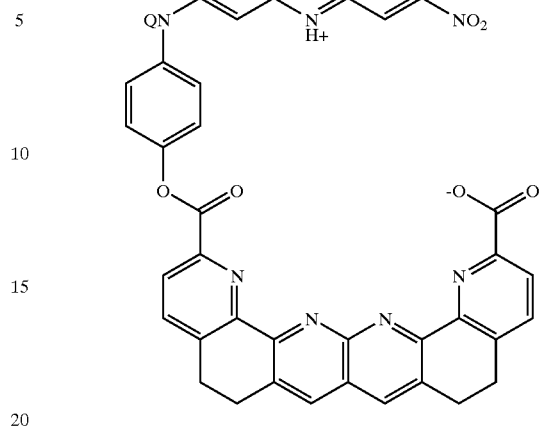
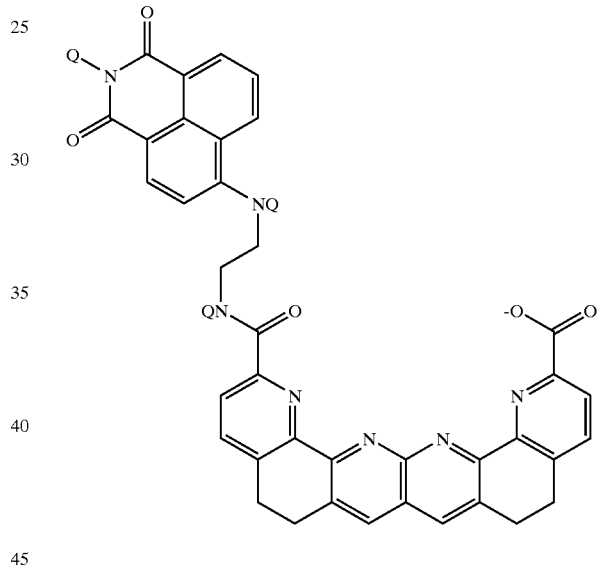
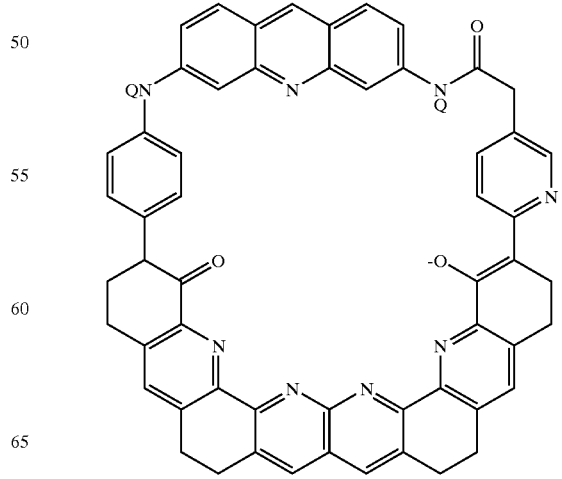

-continued

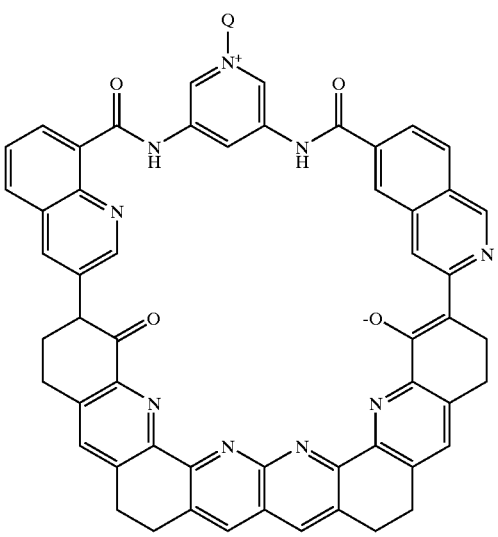

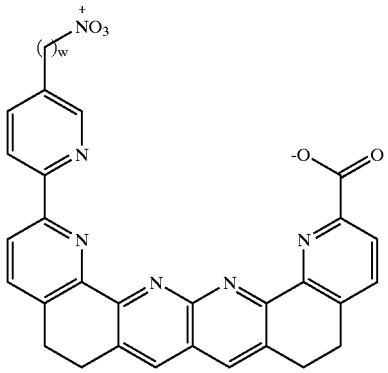

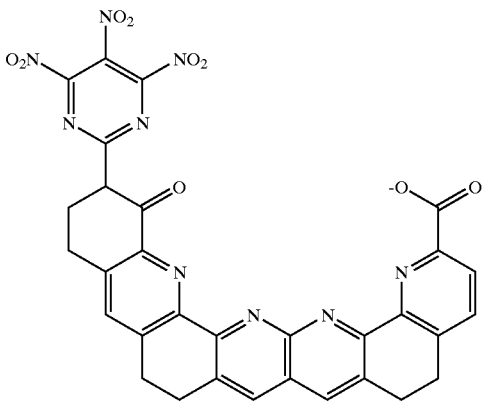

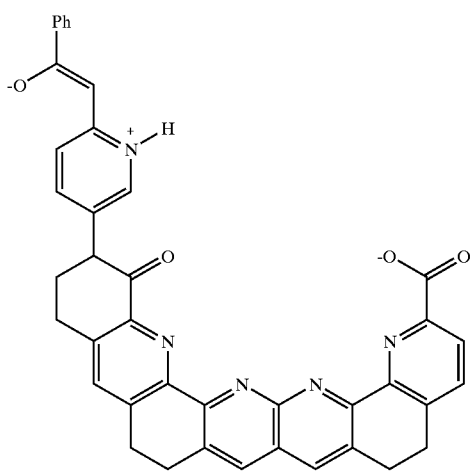

wherein Q is alkyl, alkenyl, alkynyl, aryl, or a hydrogen atom, and w and w' are integers selected such that the creatine recognizing substance is capable of performing its intended function, e.g., interact specifically a creatine compound. The values of w and w' are each individually selected integers from 0 to 10.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" moiety is an alkyl substituted with an aryl (e.g., phenylmethyl(benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to five carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "substituted" includes substituents mentioned above, which include halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

In one embodiment, the levels of the creatine compound can be directly analyzed visually, e.g., by a change in color of the creatine sensing substance and creatine compound mixture.

In one embodiment of the invention, the color, intensity or hue of the creatine sensing substance or a product thereof may be calibrated to indicate a range of creatine compound levels (e.g., the intensity of the color of the creatine sensing substance may intensify as the creatine compound level in the sample is increased; the color or hue of the creatine sensing substance may change as the creatine compound level is decreased.) In a further embodiment, the resulting mixture is analyzed by comparing the color, hue or intensity of the resulting mixture with a calibrated scale, which indicates creatine compound level in the body fluid, or, preferably, in the body. For example, the creatine compound level may be compared to the normal muscle concentration of total creatine (e.g., approximately 125 mmol/kg dry mass) (Balsom et al., 1994). In a further embodiment, the intensity of the color can be determined quantitatively, for example, by measuring changes in the optical density of a solution or by measuring the fluorescence emission.

The term "color" includes changes in the absorbance or emission radiation in the ultraviolet, visible, or infrared spectrum. Advantageously, the change in color is a change in the visible color of the creatine sensing substance. Alternatively, the change in color could be a change in the wavelength of fluorescence. Furthermore, the level of fluorescence, color or optical change may be quantified, using known spectroscopic (e.g., fluorimetric, calorimetric) techniques.

Examples of creatine recognizing substances include molecules capable of specifically interacting with creatine compounds with potentially useful changes in color, light absorption intensity or wavelength, or fluorescence emission intensity or wavelength. Such optical effects can be produced, for example, by rearrangement, transprotonation, ionization, deionization, conformational change, polarization, solvation change or electronic interaction between the creatine recognizing substance and the creatine compound. Other substances are known which generally interact with guanidinium compounds (Bell, T. W. et al. *Angew. Chem. Int. Ed.*, (1999) 38, 2543–2548).

In one embodiment, creatine recognizing substances of the invention can be designed advantageously to produce an optical signal, in addition to binding a creatine compound of interest with high affinity. This signal can be, for example, a change in light absorption or emission resulting from a structural change of the creatine recognizing substance, electronic polarization of the creatine recognizing substance, or other electronic interaction between the compound of interest and the creatine recognizing compound.

In a further embodiment, the interaction between the creatine sensing substance and the creatine compound can be detected through the use of fluorescence emission. Quenching or enhancement of emission intensity can result from energetically undemanding processes, such as electronic interaction between creatine sensing substance and the creatine compound of interest or changes in solvation of either substance upon complexation.

Heterocyclic or other fluorophores may be incorporated directly into rigid coordinating moieties of the invention and may be affected by hydrogen-bonded complexation of the creatine compound of interest. Hydrogen-bonded complexation has been shown to affect receptor fluorescence in the binding of barbituric acid derivatives by a receptor (Motesharei, K. et al. *J. Am. Chem. Soc.* (1 994) 116:7413–7414).

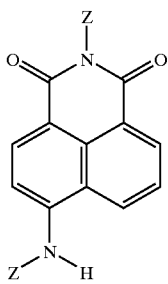

4

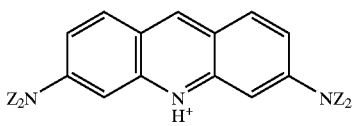

5

6

Structures 4–6 are some examples of fluorophores or chromophores that can be incorporated into creatine recognizing substances as stabilizing groups (D). It is thought that they may form somewhat weaker single hydrogen bond contacts with carboxylate, but changes in their optical properties would advantageously report the interaction between the creatine recognizing substance and the creatine compound of interest. The naphthalimide fluorophore (4) is sensitive to photo-induced electron transfer (PET), and its absorption and emission wavelengths are convenient for measurements in biological fluids (de Silva, A. P. et al. *Angew. Chem. Int. Ed. Engl.* (1995) 34:1728–1731). Acridine orange (5) can accept a proton upon creatine binding, altering absorption and emission wavelengths. In the third structure (6), a phenacetylpyridine moiety undergoes tautomerization to the dipolar structure shown, extending its absorption wavelength (Carey, A. R. E. et al. *J. Chem. Soc. Perkin Trans.* 2 (1993) 2285–2296; McCann, G. et al *J. Chem. Soc. Perkin Trans.* 2 (1997) 2761–2772).

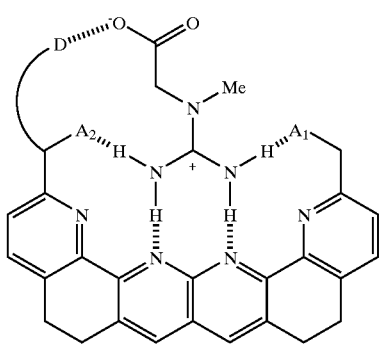

7

Substance 7 is one example of a general structure showing one conceptual approach to the design of certain creatine recognizing substances with potentially advantageous optical properties. For example, in substance 7 the cationic portion of creatine is believed to be held by hydrogen bonds to pyridine rings and to the acceptor groups ($A_1$ and $A_2$) containing, for example, oxygen or nitrogen atoms. These can be anionic or neutral groups. Either acceptor group may be linked to one or more stabilizing groups (D) which may advantageously be neutral or cationic. In 7, D may stabilize the complex by electrostatic and/or hydrogen bonding interactions with the creatine carboxylate group. Furthermore, any portion of the substance 7 may serve a second role as a chromophore or fluorophore capable of reporting, for example, an interaction between a creatine recognizing substance and a creatine compound.

Furthermore, creatine recognizing substances include, for example, members of the structural classes represented by diagrams I–VI. In these structural series of creatine recognizing substances, A is any acceptor group, as described above. Ar includes aromatic, heteroaromatic, carbocyclic or other ring or fused ring groups. The creatine recognizing substances encompassed by these series may bear any substituents which enhance or do not prohibit the ability of the creatine recognizing substance to perform its intended function. For example, substituents may aid the formation of hydrogen bonds, electrostatic contacts, or metal-ligand interactions with carboxylate groups of a creatine compound of interest. In an advantageous embodiment, the creatine recognizing substances may also comprise chromophores or fluorophores capable of optically signaling the interaction between the creatine compound of interest and the creatine recognizing substance. Furthermore, stabilizing groups (D) may also comprise chromophores or fluorophores and also may have any substituent which does not prevent the performance of the intended function of the creatine recognizing substance. In diagrams II–VI, X represents carbon, oxygen, nitrogen or sulfur. All molecules may contain any number of multiple bonds or hydrogen atoms producing stable structures. They may also bear any substituents and can be linked or fused to any other molecules. In VI, the linkage of the two X atoms by D produces a macrocyclic structure. This invention also includes macrocyclic versions of I–V and any analogues or derivatives, thereof.

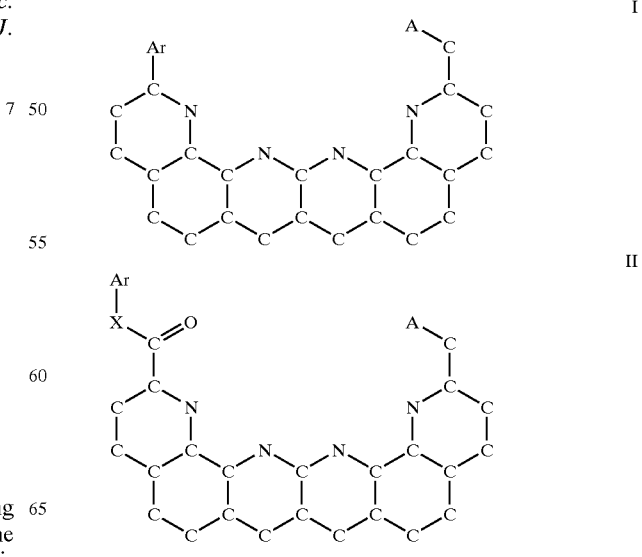

III

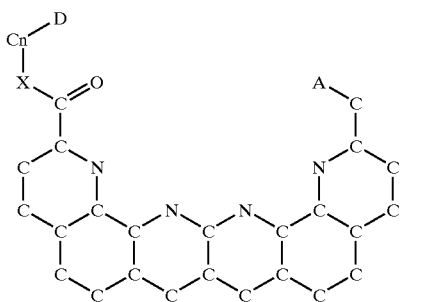

IV

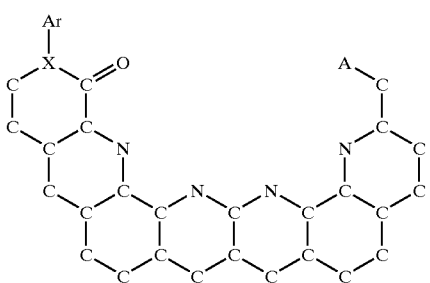

V

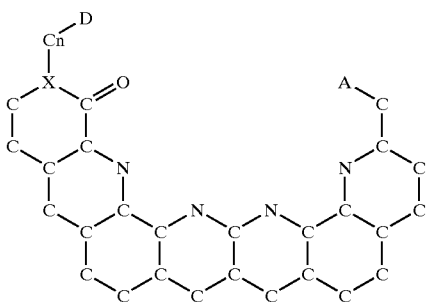

VI

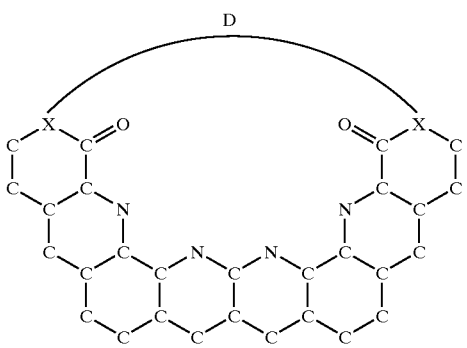

Some representative examples of creatine recognizing substances of structural classes I–VI are shown below. These examples are intended merely to illustrate some key concepts of this invention, which includes any related structures containing different stabilizing groups, acceptor groups, chromophores, fluorophores, linkers, rings, or substituents.

Substance 8 is an example of structural class I. In this particular case, the aromatic moiety (Ar) is believed to serve a dual role as a hydrogen-bond donor stabilizing group and an optical reporter. Complexation of creatine is believed to polarize the Ar group, as shown in 8-creatine, altering its light absorption and emission characteristics (Scheme 1). In substance complexes 9–11, the Ar group is a pyridine ring bearing an acetylene linker and one of the carboxylate binding groups previously discussed. These aromatic moieties may produce strong complexes and can be tailored as optical reporter groups.

Scheme 1

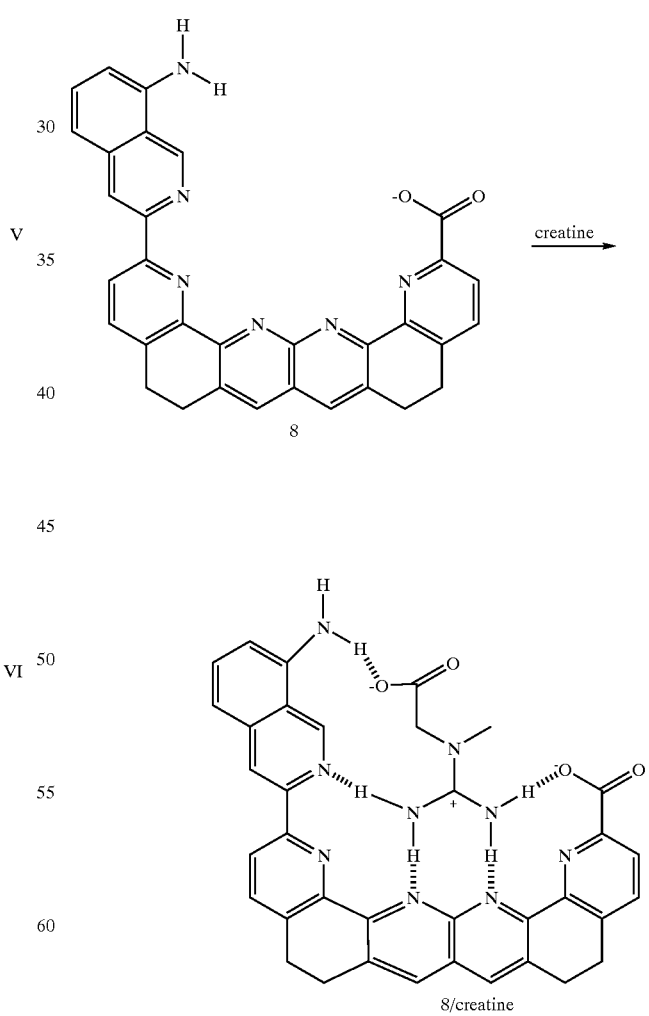

-continued

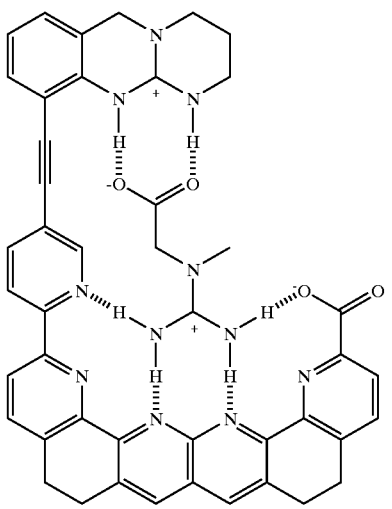

9

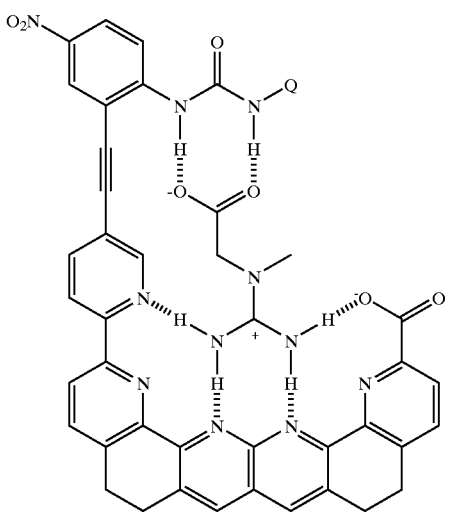

10

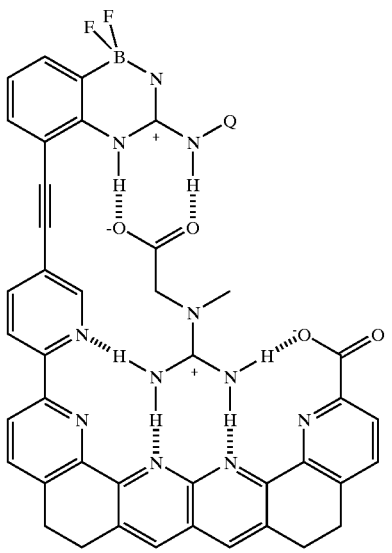

11

In structural class II, the aromatic group can be attached to an ester, amide, ketone or thioester group, which acts as a hydrogen bond acceptor for the creatine compound's guanidinium NH stabilizing group. Creatine recognizing substance complexes 12–14 illustrate examples of hydrogen bond donor stabilizing groups for the creatine compound's carboxylate group that can be linked to produce a stable complex. Substances 15 and 16 depict how a protonated dye (acridine orange) can be linked to substances of type II to produce an electrostatic contact with the carboxylate of a creatine compound. In media of suitable polarity, creatine binding may be accompanied by dye protonation, causing a pronounced change in color and fluorescence.

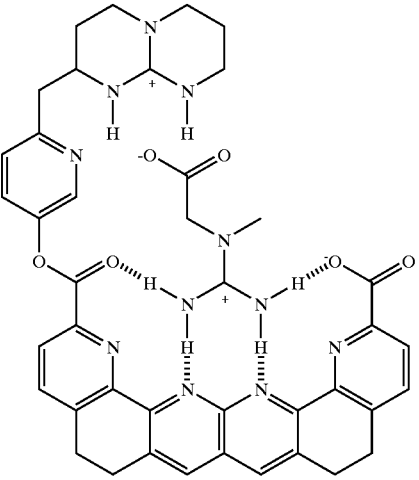

12

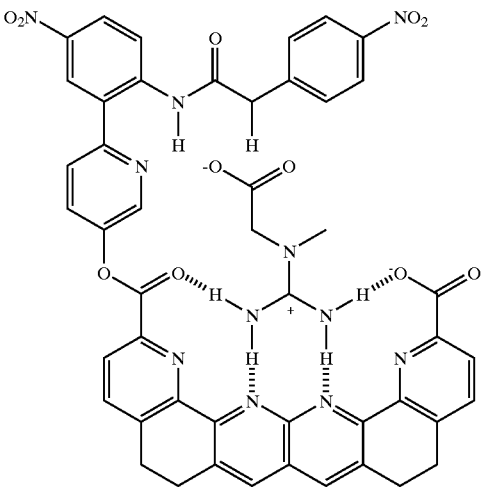

13

-continued

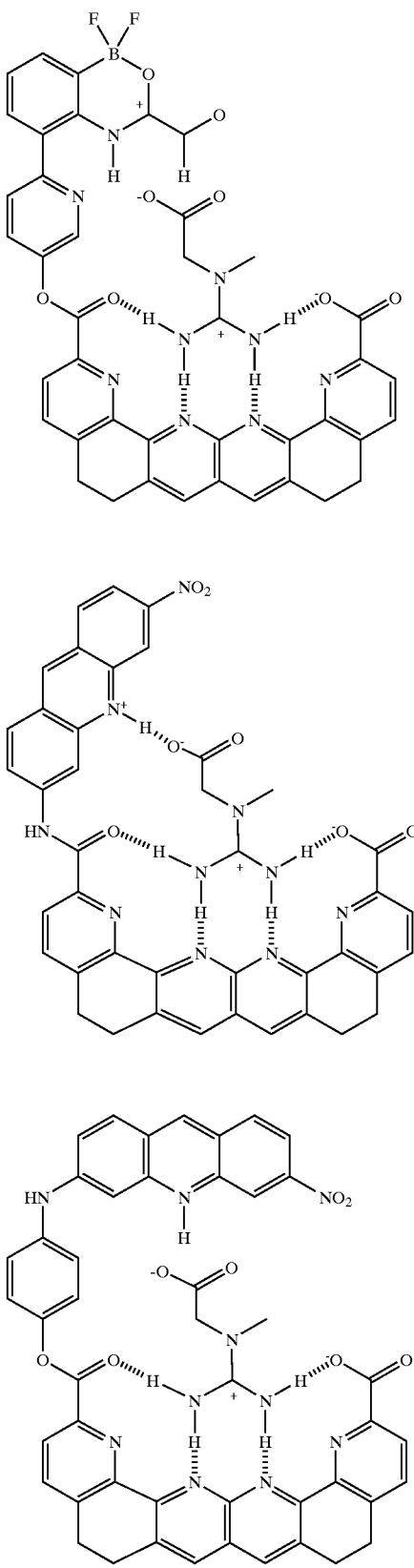

Substance complexes 17 and 18 depict flexible linkers which can be used to tether a known or novel fluorophore to creatine recognizing substances. In 17, the naphthalimide fluorophore is tethered by a 2-carbon chain, while in 18 a 3-carbon chain is used. In both cases, the naphthalimide NH group can act as a hydrogen-bond donor stabilizing group for the creatine compound's carboxylate group. This anion may behave as an effective PET quencher for the sensitive naphthalimide fluorophore.

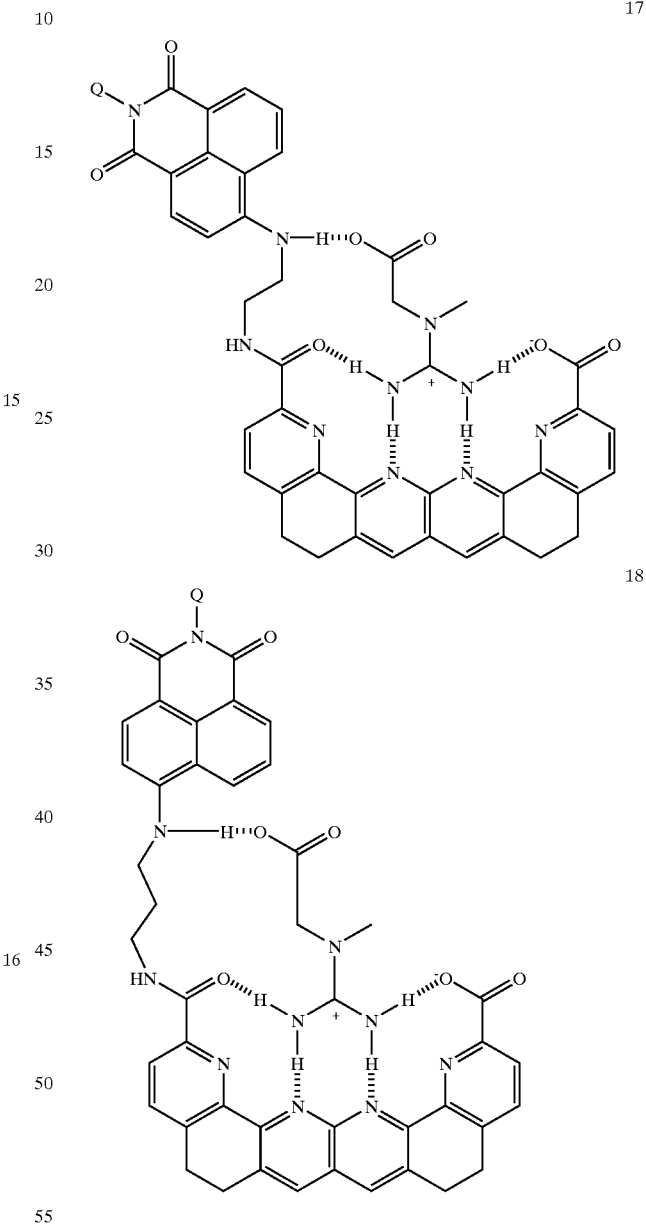

In Scheme 2, substance 19 is an example of structural class IV, in which a stabilizing group may be attached to a cyclic, carbonyl acceptor group on the left side of the molecule. In media of appropriate polarity, binding of creatine may cause tautomerization of the arylacylquinoline moiety to produce the dipolar structure shown in 19-creatine. Extended electronic delocalization in this complex may cause light absorption and fluorescence to occur at longer wavelengths, producing an analytically useful optical signal.

Scheme 2

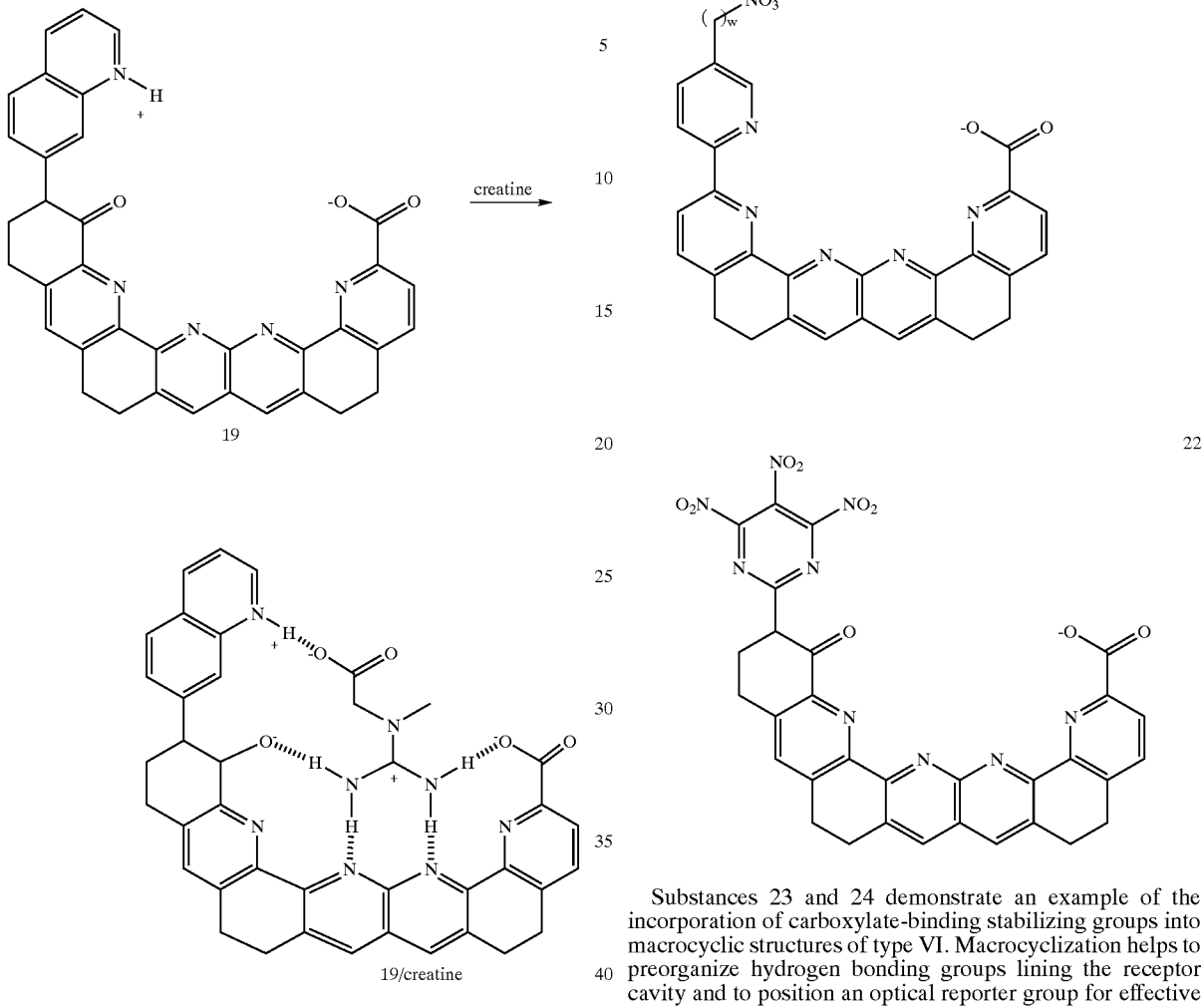

Other substances incorporating stabilizing D group modifications include compounds 20–22, shown below.

Substances 23 and 24 demonstrate an example of the incorporation of carboxylate-binding stabilizing groups into macrocyclic structures of type VI. Macrocyclization helps to preorganize hydrogen bonding groups lining the receptor cavity and to position an optical reporter group for effective communication with the creatine compound. These complexes also employ the arylacylpyridine tautomerization strategy, but many other structural variations can be envisioned.

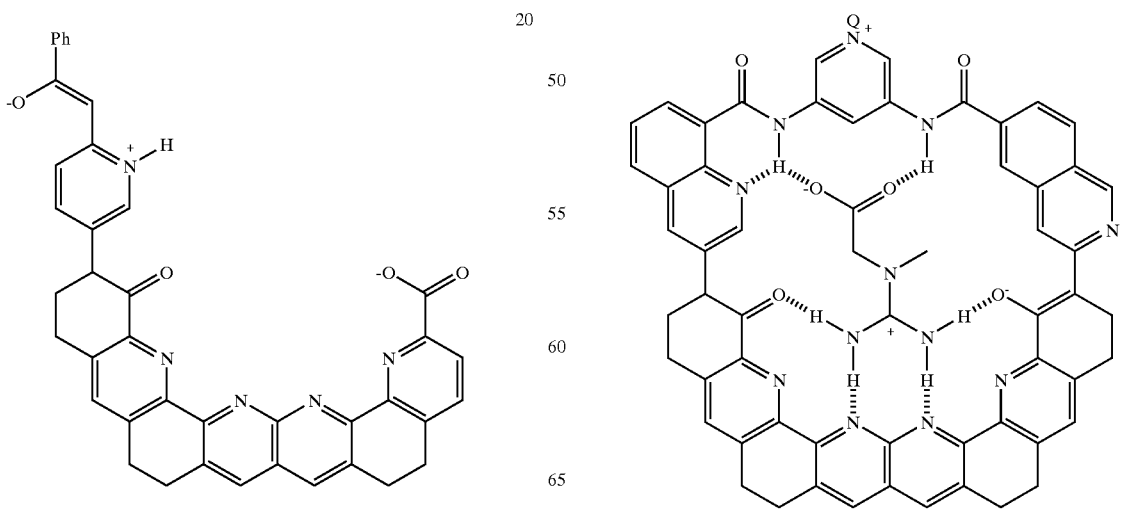

-continued
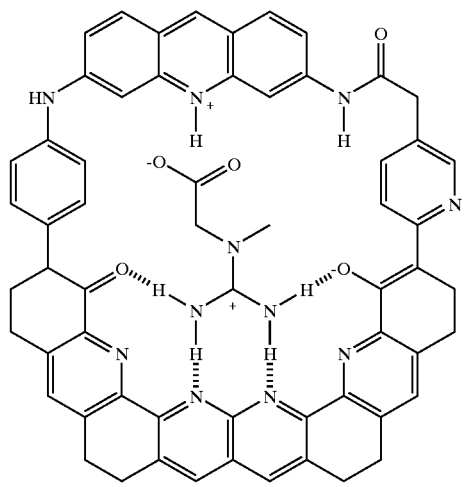
24
Other macrocyclic structures include 25 and 26, shown below:
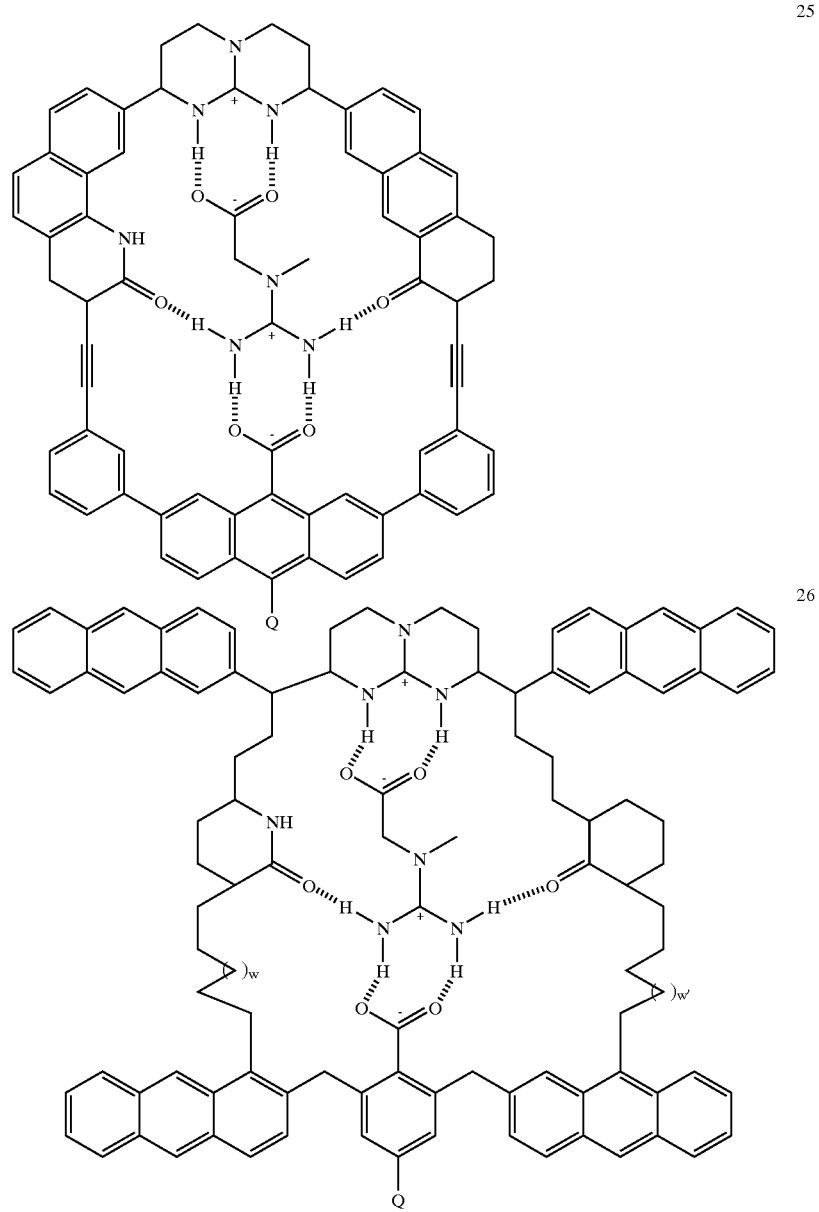

wherein w and w' are each independently from about 0 to 15 and Q is hydrogen, halogen, alkyl, alkenyl, alkynyl, aryl, or another advantageous substituent.
Other creatine recognizing substances deviate from groups I–VI by having other rigid coordinating moieties. Examples of some of these substances are shown in structures 26–34.
26
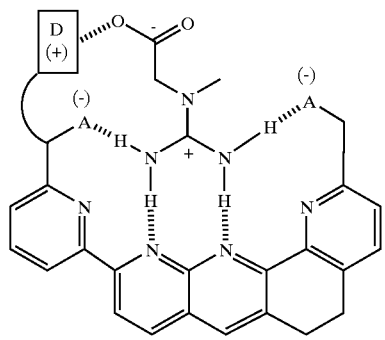
27
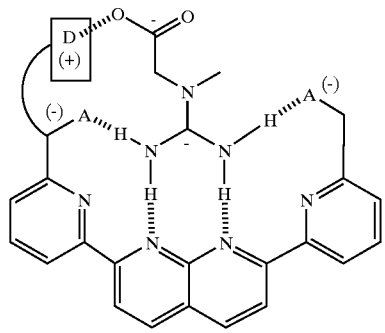
28
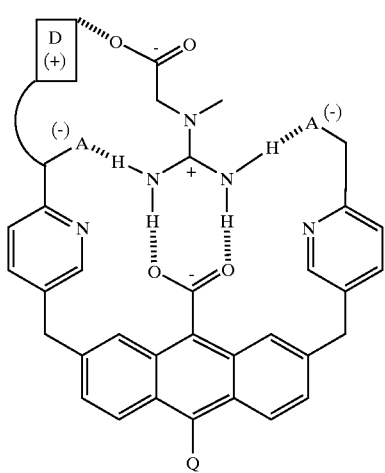
29
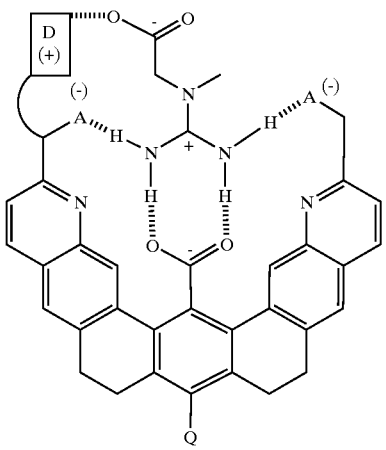
30
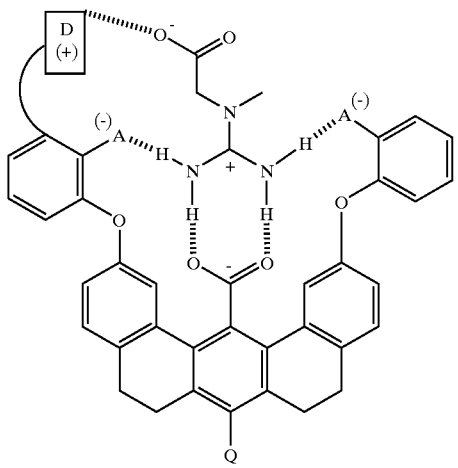
31
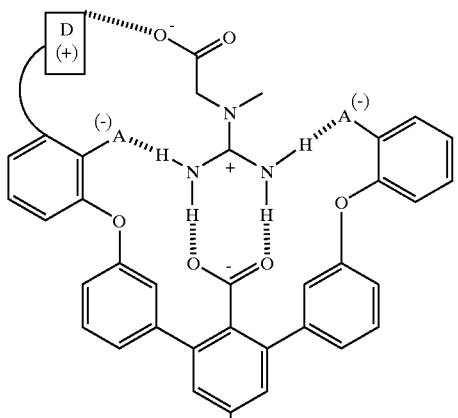

-continued

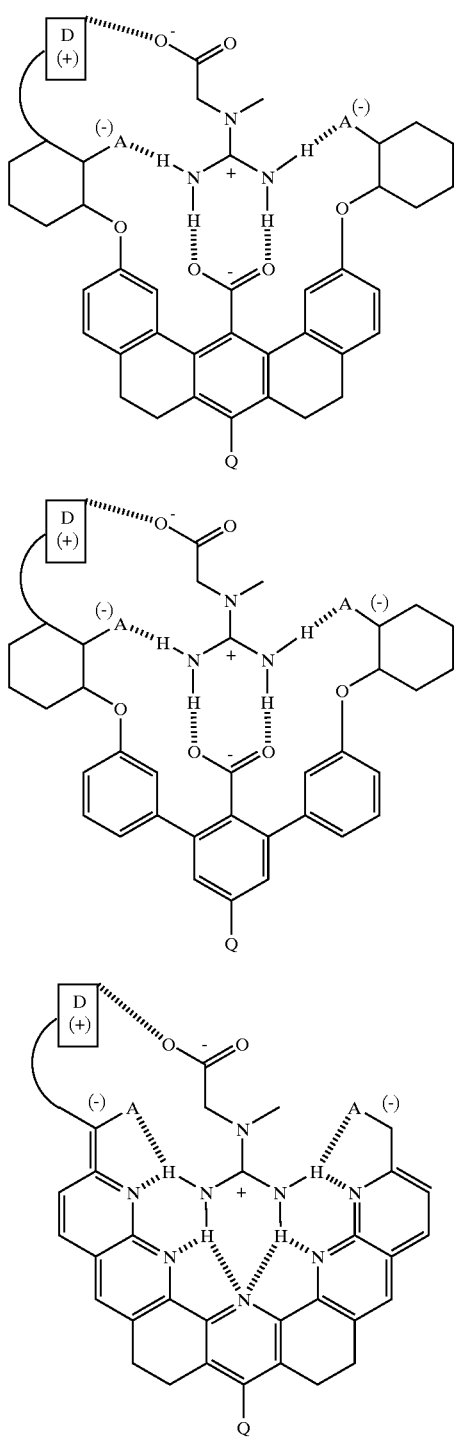

In a further embodiment, the method also comprises the step of administering a therapeutically effective amount of a creatine compound to increase creatine compound levels in a subject from which the body fluid sample was taken. In a particularly preferred embodiment, the creatine, creatinine, and/or total creatine level is determined in a sample, analyzed, and then if the level is found to be below the desired level, a therapeutically effective amount of a creatine compound is administered.

The term "administering" includes routes of administration which allow the creatine compound to perform its intended function. Examples of routes of administration which can be used include parental injection (e.g., subcutaneous, intravenous, and intramuscular), intraperitoneal injection, oral, inhalation, and transdermal. The injection can be bolus injections or can be continuous infusion. Depending on the route of administration, the creatine compound can be coated with or disposed in a selected material to protect it from natural conditions which may detrimentally effect its ability to perform its intended function. The creatine compound can be administered alone or with a pharmaceutically acceptable carrier. Further, the creatine compound can be administered as a mixture of creatine compounds, which also can be coadministered with a pharmaceutically acceptable carrier. Preferably the creatine compounds are administered orally.

The phrase "pharmaceutically acceptable carrier" includes pharmaceutically acceptable materials, compositions or vehicles, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The language "therapeutically effective amount" includes the amount of the creatine compound sufficient to prevent onset of diseases or significantly reduce progression of such diseases in the subject being treated. A therapeutically effective amount can be determined on an individual basis and will be based, at least in part, on consideration of the severity of the symptoms to be treated and the activity of the specific analog selected if an analog is being used. Further, the effective amounts of the creatine compound may vary according to the age, sex and weight of the subject being treated. Thus, a therapeutically effective amount of the creatine compound can be determined by one of ordinary skill in the art employing such factors as described above using no more than routine experimentation in clinical management. This therapeutic amount will be linked to levels of creatine compound detected in the assay kit proposed in this invention.

In another embodiment, the invention features a portable kit for determining creatine compound levels in a body fluid. In one embodiment, the kit comprises a creatine sensing substance and instructions for use. The kit may also include a container, vials for the bodily fluids, solvents, and creatine compounds in therapeutically effective amounts.

Although methods for determining creatine and creatinine levels are currently available, these methods are not suitable for use in a kit. For example, one method currently used for determining creatine and creatinine levels separately is high-performance liquid chromatography (HPLC) (see, Dunnett, el al. *Scand. J. Clin. Lab. Invest.* (1991) 51:137–141; Werner et al. *J. Chromatogr.* (1990) 525:265–275; Hung et al. *J. Chromatograph.* (1984) 305:281–294). Other known assays include enzymatic assays specific for creatine (Okumiya et al. *Clin. Chem.* (1998) 44:1489–1496; Motonaka et al. *Anal. Lett.* (1990) 23(11):1981–1991; Harris et al. *Scand. J. Clin. Lab. Invest.* (1974)33:109–120; and Delanghe et al. *Fresnius Z. Anal. Chem.* (1988)330:366–367) and for both creatinine and creatine (see, Kinoshita et al. *Electroanalysis* (1997) 9(16):1234–1238; and Benedict *J. Biol. Chem.* (1914) 18:191–193). These methods are not suitable for use in a kit because they depend the extensive use of laboratory equipment.

In a preferred embodiment, the creatine sensing substance is associated with a solid support, e.g., embedded in a carrier matrix. Advantageously, the carrier matrix is insoluble in water and other physiological fluids. Examples of carrier matrices include: paper, sponge materials, cellulose, wood, woven and nonwoven fabrics, glass fiber, polymeric films, preformed and microporous membranes, synthetic and modified naturally-occurring polymers, or hydrophilic inorganic powders.

In a further embodiment, the solid support is a creatine compound sensing substance embedded test strip. The test strip may include a support strip, or handle, normally constructed from a hydrophobic plastic, and a reagent test region, containing a bibulous or a nonbibulous carrier matrix incorporating the creatine sensing substance. In one embodiment, the carrier matrix is an absorbent material that allows the body fluid to move, in response to capillary forces, through the carrier matrix to contact the creatine sensing substance and produce a detectable or measurable color transition. In the assay of a whole blood sample, the carrier matrix generally is not permeable to the cellular material. Therefore, the highly-colored cells can be wiped or blotted from the test pad and not interfere with or mask the assay for the creatine compound. Furthermore, if the carrier matrix is permeable to the cellular material, persons of ordinary skill in the art are aware of techniques and devices to separate the cellular material from the test sample to eliminate the interfering affects of the cellular material.

The carrier matrix can be any substance capable of incorporating the creatine sensing substances, as long as the carrier matrix is substantially inert, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like celulosic beads, and especially fiber-containing papers such as filter paper or chromatographic paper; synthetic or modified naturally-occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness.

This invention is further illustrated by the following examples which should not be construed as limiting. The contents of all references and published patents and patent applications cited throughout the application are hereby incorporated by reference.

EXEMPLIFICATION OF THE INVENTION

Example 1

Synthesis of Certain Creatine Sensing and/or Creatine Recognizing Substances of the Invention The following example is an example of a general synthetic method which can be used to synthesize certain creatine sensing and/or creatine recognizing substances of the invention. The synthetic method is shown below in Scheme 3.

Creatine sensing substance 42 was synthesized in seven steps as the dipotassium salt (Bell, T. W. et al. *Angew. Chem.*

*Int. Ed,* (1999) 38, 2543–2548). The benzene ring of quinaldine (35) was selectively reduced by catalytic hydrogenation with palladium-on-carbon in trifluoroacetic acid. Condensation of 36 with benzaldehyde in acetic anhydride gave dibenzylidene derivative 37, which was conveniently purified by vacuum distillation. Ozonolysis of 37 gave ketoaldehyde 38, which underwent the Jones oxidation to ketoacid 39. Friedländer condensation of 39 with 4-aminopyrimidine-5-carboxyaldehyde gave pyrimidine 40. The pyrimidine 40 was then hydrolyzed to aminoaldehyde 41. A second condensation of 39 with 41 gave creatine sensing substance, 42. The substance 42 was purified by recrystallization and obtained in 18% overall yield from quinaldine. The molecular symmetry of 42 results from the use of the same ketone (39) in both Friedländer condensations. However, two different ketones could be used to make unsymmetrical creatine sensing and/or recognizing substances, which could bear additional moieties, such as, stabilizing and acceptor groups.

The ability of substance 42 to detect creatine was evaluated by $^1$H NMR spectroscopy. The interaction of creatine with substance 42 was detected in a $CD_3OD$ solution, by the downfield shift of most of substance 42's $^1$H spectroscopy signals upon addition of creatine to the test solution. (Bell, T. W. et al. 36$^{th}$ National Organic Symposium, U. of Wisconsin, Madison, Wis., Jun. 13, 1999–Jun. 17, 1999).

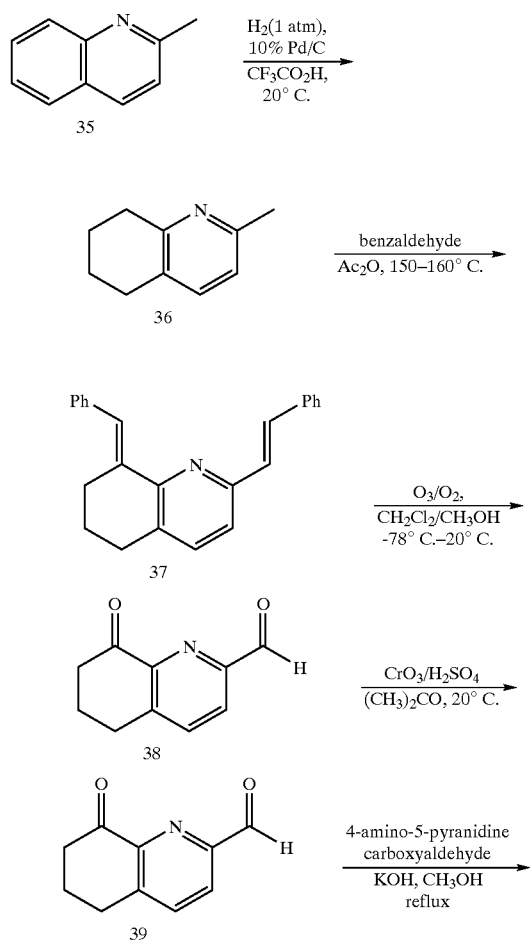

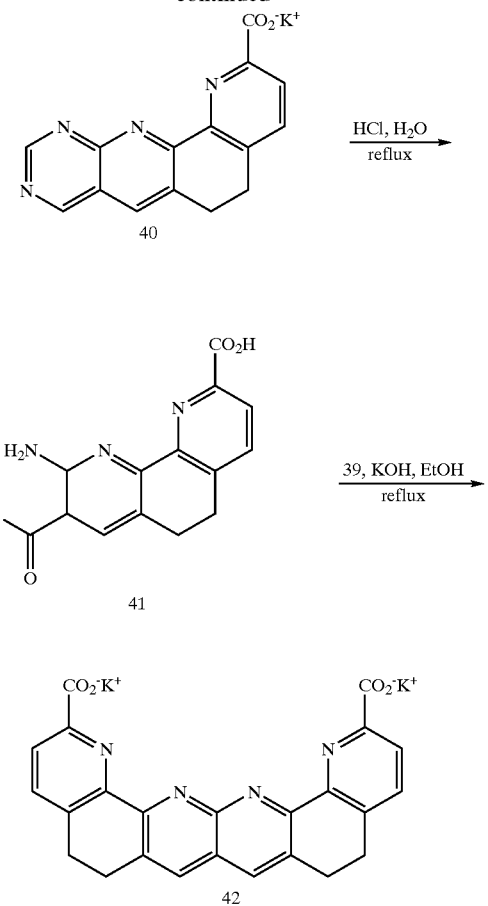

Example 2
Determining the Level of a Creatine Compound in a Body Fluid

This example discusses how a creatine recognizing substance can be used to detect creatine in a body sample.

A creatine recognizing substance is dissolved in chloroform (0.14 mM). Creatine obtained from commercial sources is dissolved in water at concentrations between about 0 μM to about 50 μM (0.1 mL, pH 6.0, 0.1 M MES buffer). The organic and aqueous solutions are shaken and the chromogenic response of the creatine recognizing substance is measured at each concentration.

A body sample of saliva is taken from a patient. The saliva is diluted with an equal volume of water. The pH of the solution is adjusted and 0.1 M MES buffer is added. 0.1 mL of the solution is added to the 0.14 mM solution of creatine recognizing substance in chloroform. The mixture is shaken and the chromogenic response of the creatine recognizing substance is measured and compared to the curve generated above.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for determining creatine compound levels in a body sample of a subject, comprising:
   contacting a body sample with a creatine recognizing substance; and analyzing the resulting mixture, such that creatine compound levels are determined, wherein said creatine recognizing substance is of formula (I):

$$RD_nA_m \quad (I)$$

wherein

R is a rigid coordinating moiety;

D is each an independently selected stabilizing group;

A is each an independently selected acceptor group; and n and m are independently selected integers from 0 to 10.

2. The method of claim 1, wherein said body sample is a body tissue.

3. The method of claim 2, wherein said body tissue is a tissue which utilizes the creatine kinase energy system.

4. The method of claim 3, wherein said body tissue is selected from the group consisting of muscle, brain, nervous system, retina, and kidney tissues.

5. The method of claim 1, wherein said body sample is a body fluid.

6. The method of claim 1, wherein said body fluid is selected from the group consisting of urine, blood, saliva, sweat, and spinal and brain fluids.

7. The method of claim 5, further comprising obtaining said body fluid non-invasively.

8. The method of claim 1, wherein said creatine recognizing substance is an organic small molecule.

9. The method of claim 1, wherein the creatine recognizing substance is selected from the group consisting of the following:

10. The method of claim 1, wherein said creatine recognizing substance is of formula (II):

wherein $A_1$ and $A_2$ are each independently selected acceptor groups;

D is a stabilizing group; and

R is a rigid coordinating moiety.

11. The method of claim 10, wherein said rigid coordinating moiety is multicyclic.

12. The method of claim 10, wherein said rigid coordinating moiety comprises at least one heterocycle.

13. The method of claim 10, wherein said rigid coordinating moiety is selected from the group consisting of:

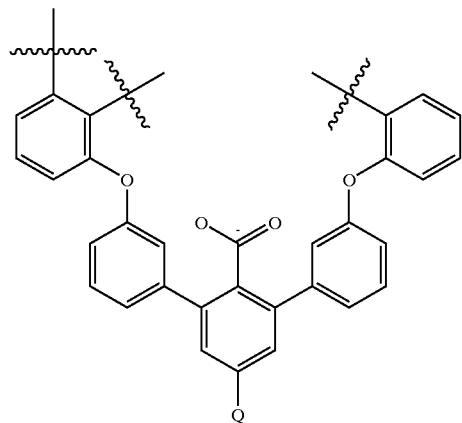

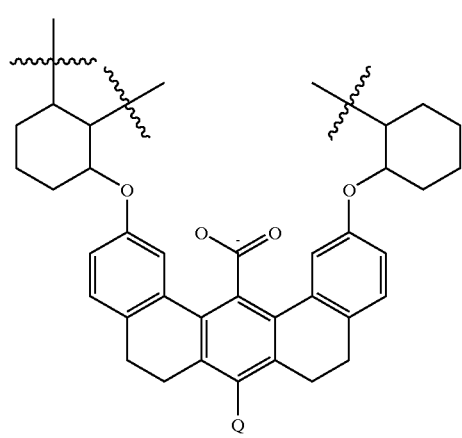

-continued

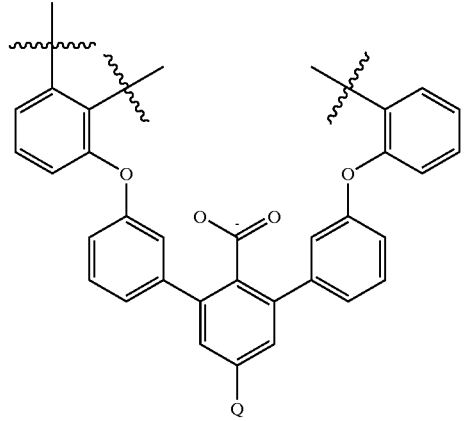

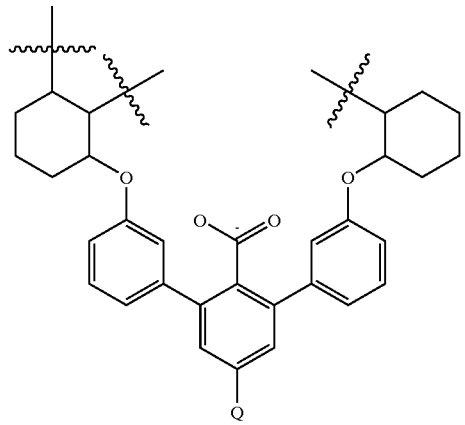

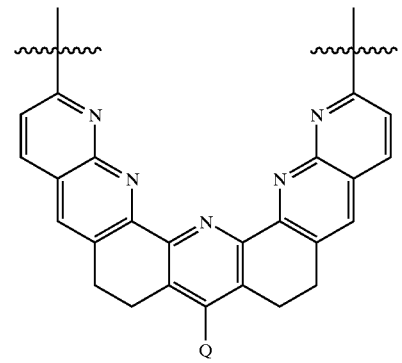

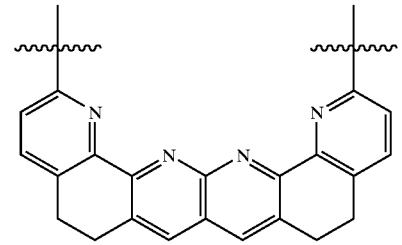

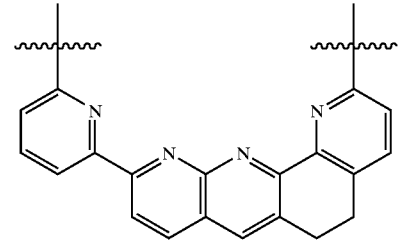

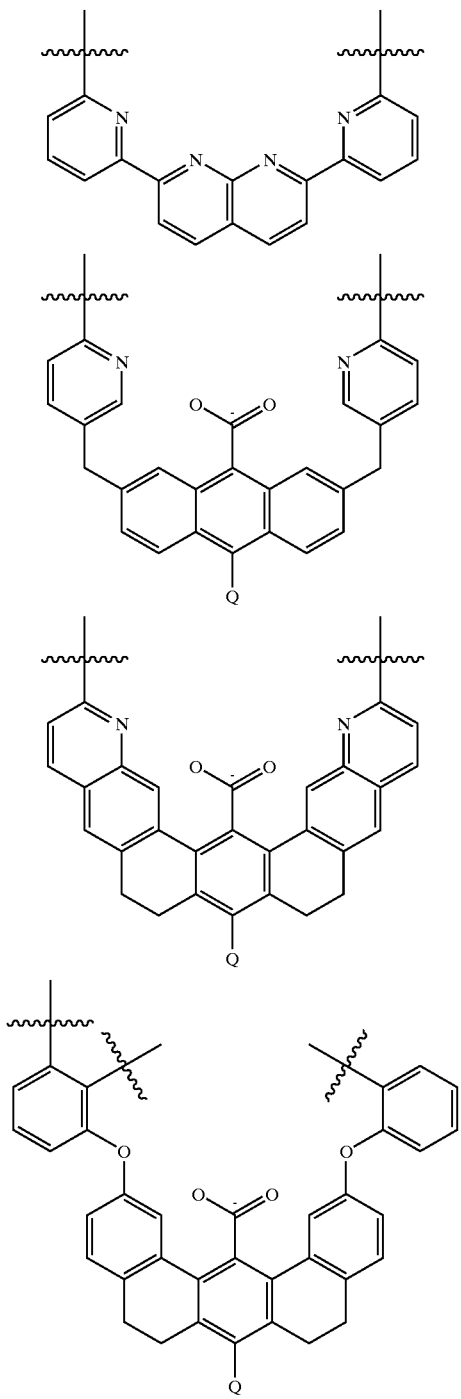

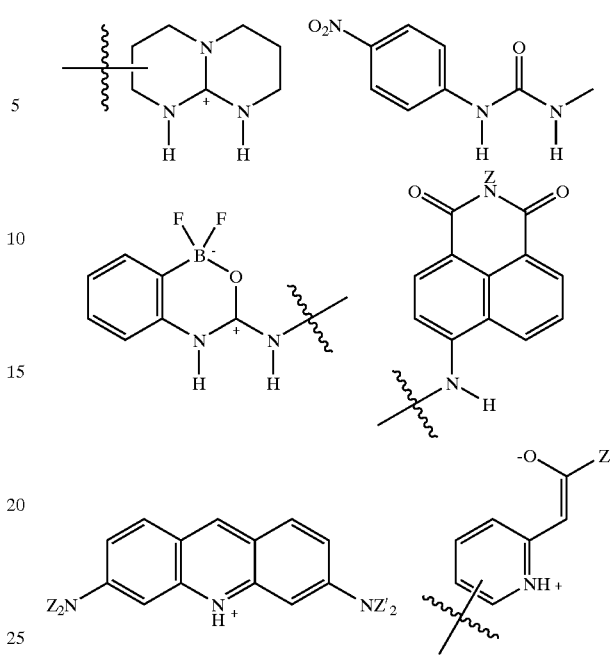

wherein Z and Z' are each independently selected from the group consisting of alkyl, aryl, alkenyl, alkynyl moieties and hydrogen and halogen atoms.

21. The method of claim 10, wherein said creatine recognizing substance is selected from the group consisting of:

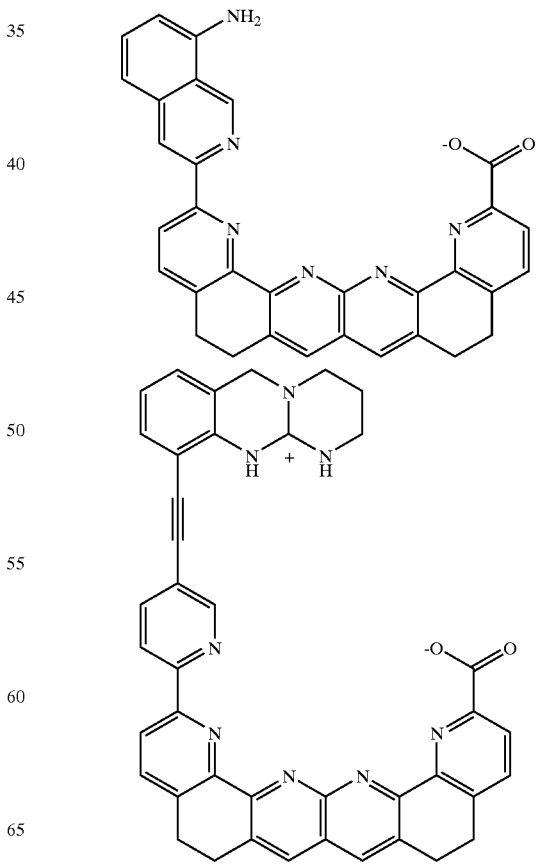

wherein Q is selected from the group consisting of alkyl, aryl, alkenyl, alkynyl moieties and hydrogen atoms.

14. The method of claim 10, wherein $A_1$ and $A_2$ are anionic or neutral.

15. The method of claim 10, wherein $A_1$ and $A_2$ are capable of forming hydrogen bonds with a creatine compound.

16. The method of claim 14, wherein $A_2$ is carboxylate.

17. The method of claim 14, wherein $A_1$ is a carbonyl moiety or heterocyclic.

18. The method of claim 10, wherein D is neutral or cationic.

19. The method of claim 10, wherein D comprises at least one nitrogen containing group.

20. The method of claim 18, wherein D is selected from the group consisting of:

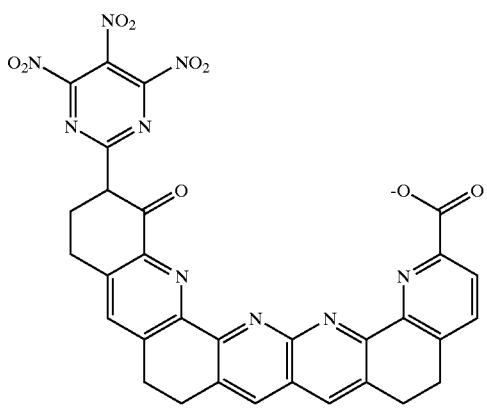
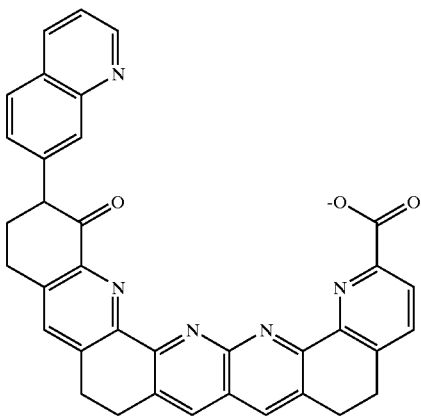
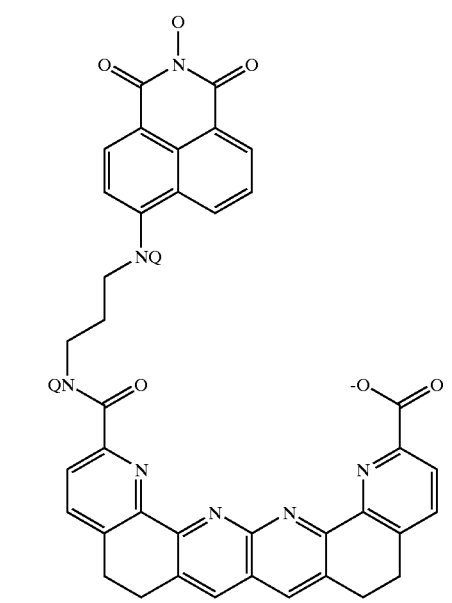
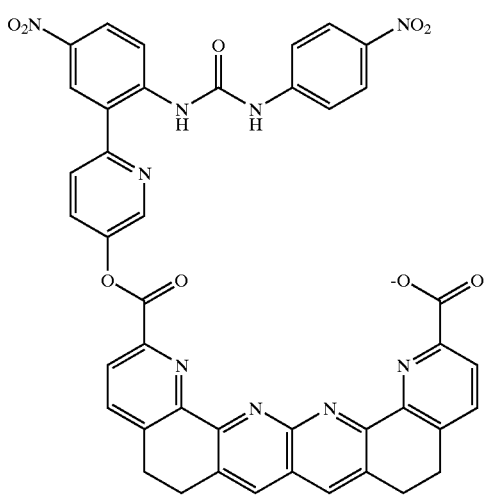
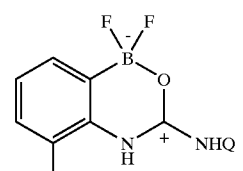
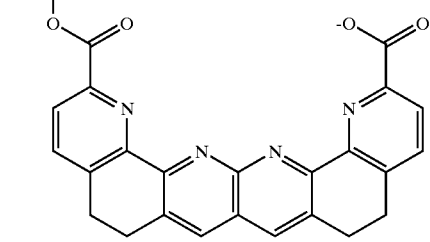

51
-continued
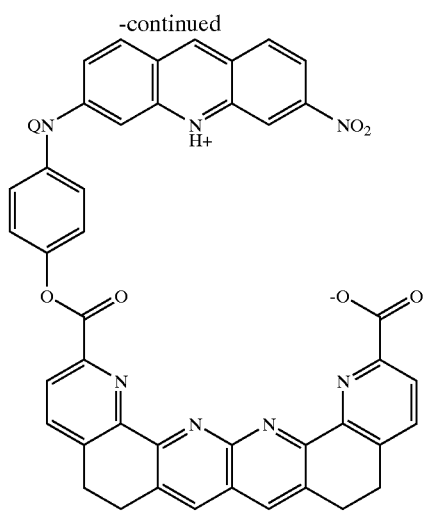
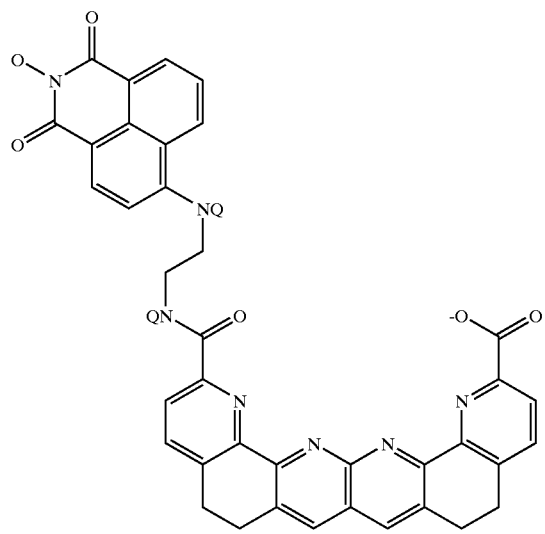
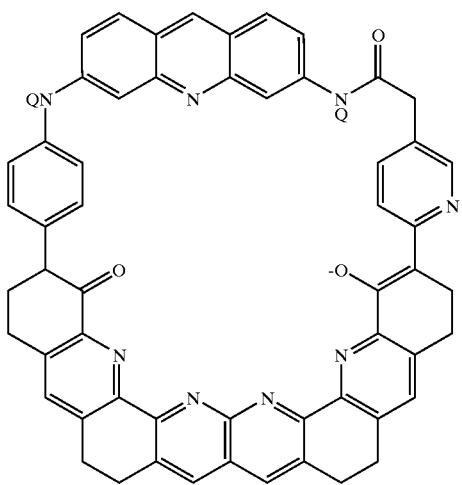
52
-continued
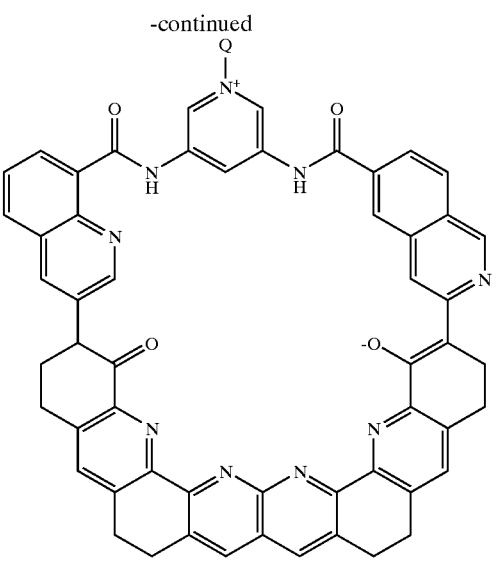
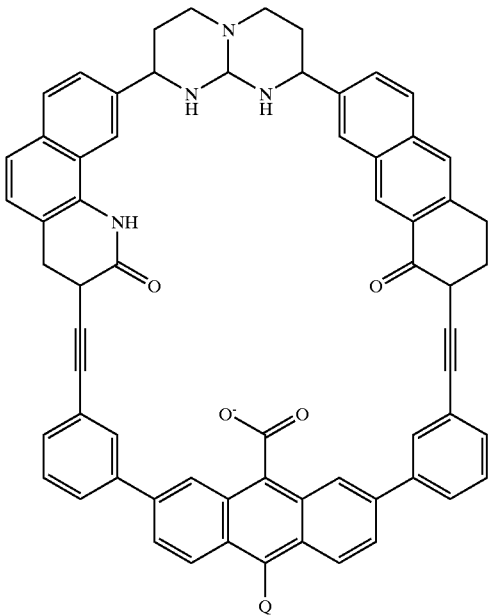
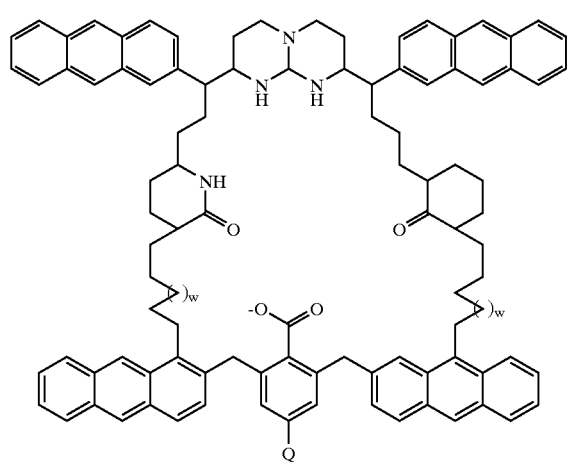

-continued

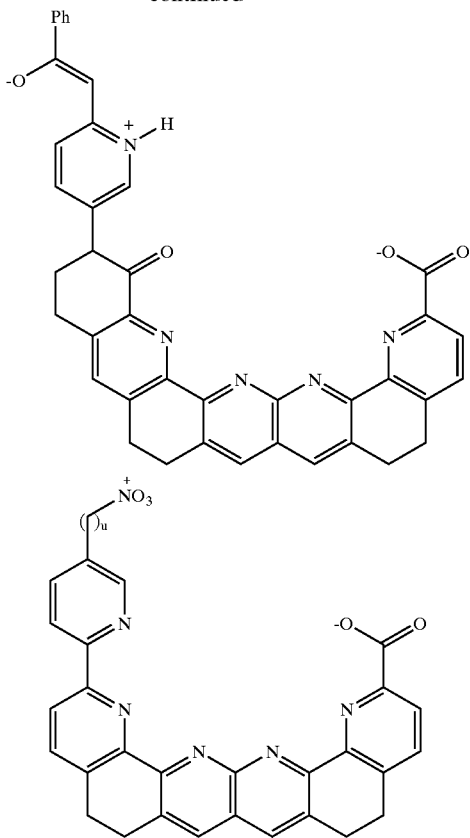

wherein
Q is hydrogen, alkyl, alkenyl, alkynyl, or aryl; and
w and w' are each independently selected intergers from 0 to 10.

22. The method of claim 1, wherein said creatine compound levels can be directly analyzed visually.

23. The method of claim 1, wherein said creatine recognizing substance changes color upon contacting the creatine compound.

24. The method of claim 1, further comprising administering a therapeutically effective amount of a creatine compound to a subject to increase the creatine compound level in said subject.

25. The method of claim 1, wherein said creatine compound is creatine.

26. The method of claim 1, wherein said creatine compound is creatine phosphate.

27. The method of claim 1, wherein said creatine compound is creatinine.

28. The method of claim 1, wherein said subject is a human.

29. A method for comparing creatine and creatinine levels in a body fluid, comprising:

contacting the body fluid with a creatine recognizing substance;

contacting the body fluid with a creatinine sensing substance; and analyzing the resulting mixture, such that creatine and creatinine levels are compared, wherein said creatine recognizing substance is of formula (I):

$$RD_nA_m \qquad (I)$$

wherein

R is a rigid coordinating moiety;

D is each an independently selected stabilizing group;

A is each an independently selected acceptor group; and n and m are independently selected integers from 0 to 10.

30. The method of claim 29, wherein the body fluid is contacted with the creatine recognizing substance and the creatinine sensing substance separately.

31. The method of claim 29, wherein the body fluid is from a subject suffering from kidney dysfunction.

32. The method of claim 29, wherein the body fluid is from a subject to whom creatine was previously administered.

33. The method of claim 21, wherein said creatine recognizing substance is:

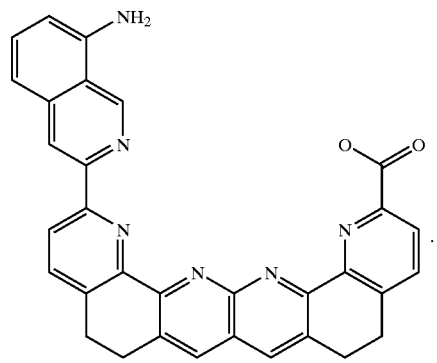

* * * * *